(12) United States Patent
Weinberg et al.

(10) Patent No.: US 10,448,856 B2
(45) Date of Patent: *Oct. 22, 2019

(54) METHOD AND SYSTEM TO DISCRIMINATE RHYTHM PATTERNS IN CARDIAC ACTIVITY

(71) Applicant: Pacestter, Inc., Sylmar, CA (US)

(72) Inventors: Lisa P. Weinberg, Moorpark, CA (US); Pritika Toutam, Winnetka, CA (US)

(73) Assignee: PACESETTER, INC., Sylmar, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/924,722

(22) Filed: Mar. 19, 2018

(65) Prior Publication Data

US 2018/0206753 A1 Jul. 26, 2018

Related U.S. Application Data

(63) Continuation of application No. 15/084,373, filed on Mar. 29, 2016, now Pat. No. 9,949,660.

(51) Int. Cl.
*A61B 5/0464* (2006.01)
*A61B 5/04* (2006.01)
(Continued)

(52) U.S. Cl.
CPC ............ *A61B 5/0464* (2013.01); *A61B 5/046* (2013.01); *A61B 5/04012* (2013.01);
(Continued)

(58) Field of Classification Search
CPC . A61B 5/0664; A61B 5/04012; A61B 5/0452; A61B 5/046; A61B 5/6869; A61B 5/7221; A61B 5/0022; G06F 19/30
See application file for complete search history.

(56) References Cited

U.S. PATENT DOCUMENTS 7,389,142 B2 6/2008 Holmstrom
8,135,456 B2 3/2012 Haluska
(Continued)

OTHER PUBLICATIONS

Restriction Requirement, dated Apr. 17, 2017—U.S. Appl. No. 15/084,373.
(Continued)

*Primary Examiner* — Paula J Stice

(57) ABSTRACT

Methods and systems are provided for discriminating rhythm patterns in cardiac activity. The method and system obtain cardiac activity data for multiple cardiac beats over a predetermined period of time. Multi-beat segments within the cardiac activity data exhibit different rhythm patterns of interest including fast and slow rhythm patterns. The method and system calculate a cardiac beats timing relation representative of intervals between the cardiac beats within a measurement window, wherein the measurement window is configured to overlap the corresponding multi-beat segment. The method and system designate the cardiac beats timing relation to have one of the rhythm patterns of interest based on a rate threshold, identifies when successive multi-beat segments exhibit rhythm patterns that transition between the fast and slow irregular rhythm patterns and records the irregular rhythm pattern transition in connection with the cardiac activity data.

12 Claims, 14 Drawing Sheets

(51) Int. Cl.
    *A61B 5/0452*     (2006.01)
    *A61B 5/00*     (2006.01)
    *A61B 5/046*     (2006.01)
    *G06F 19/00*     (2018.01)

(52) U.S. Cl.
    CPC .......... *A61B 5/0452* (2013.01); *A61B 5/6869* (2013.01); *A61B 5/7221* (2013.01); *A61B 5/0022* (2013.01); *G06F 19/30* (2013.01)

(56) References Cited

U.S. PATENT DOCUMENTS

| | | |
|---|---|---|
| 8,241,221 B2 | 8/2012 | Park |
| 2009/0264783 A1 | 10/2009 | Xi et al. |

OTHER PUBLICATIONS

NonFinal Office Action, dated Jun. 29, 2017—U.S. Appl. No. 15/084,373.
Final Office Action, dated Oct. 6, 2017—U.S. Appl. No. 15/084,373.
Notice of Allowance, dated Dec. 27, 2017—U.S. Appl. No. 15/084,373.

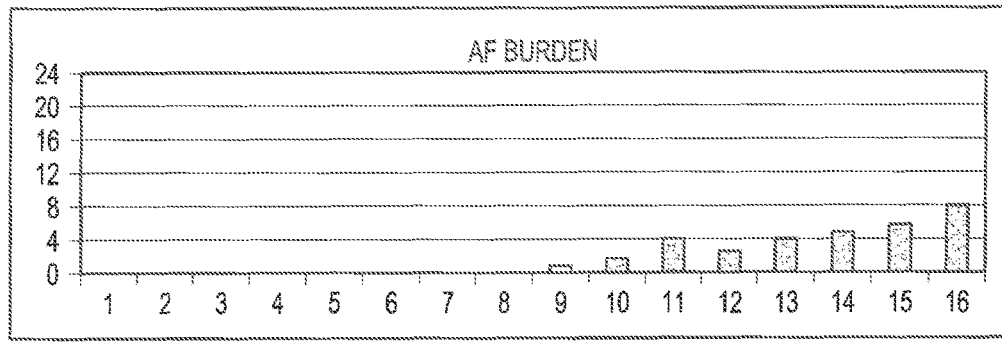
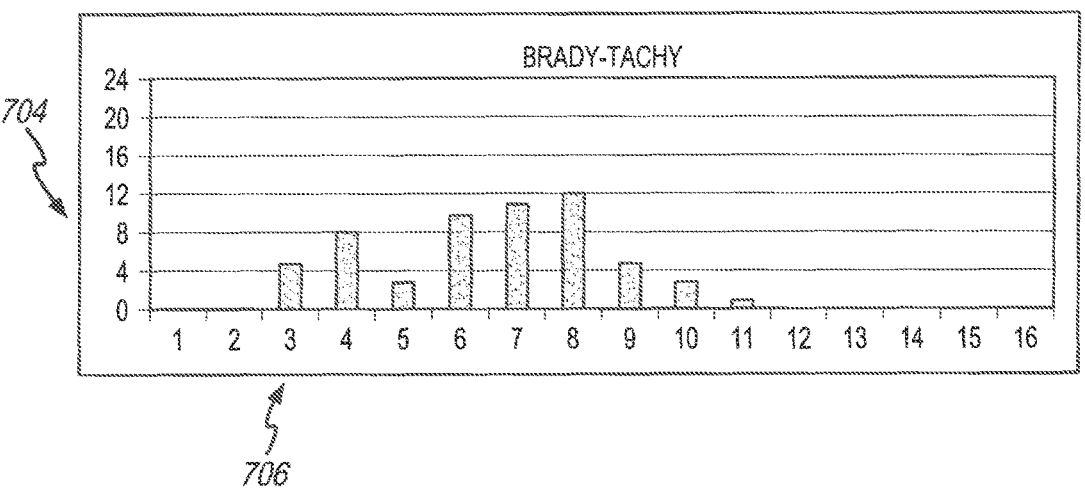
FIG. 7

METHOD AND SYSTEM TO DISCRIMINATE RHYTHM PATTERNS IN CARDIAC ACTIVITY

CROSS REFERENCE TO RELATED APPLICATIONS

This application is a continuation of U.S. patent application Ser. No. 15/084,373, filed Mar. 29, 2016.

FIELD OF THE INVENTION

Embodiments herein relate generally to implantable medical devices, and more particularly to an implantable loop recorders for monitoring cardiac events such as heart rate and rhythm.

BACKGROUND OF THE INVENTION

Embodiments herein generally relate to detection and discrimination of rhythm patterns of interest, and more particularly to discriminating Tachy-Brady Syndrome episodes from atrial fibrillation episodes.

Atrial fibrillation (AF) is a common and serious cardiac arrhythmia, affecting more than two million people in the United States alone. Clinically, atrial fibrillation involves an abnormality of electrical impulse formation and conduction that originates in the atria. Atrial fibrillation is characterized by multiple swirling wavelets of electrical current spreading across the atria in a disorganized manner. The irregularity of electrical conduction throughout the atria creates irregular impulse propagation through the atrioventricular (AV) node into the ventricle.

Impulse propagation through the AV node may be extremely rapid, leading to reduced diastolic filling of the heart chambers and a corresponding reduction of the cardiac pumping action. Increased heart rate and loss of AV synchrony may also exacerbate any underlying heart problems, such as heart failure, coronary blood flow, or other pulmonary disorders. Alternatively, impulse propagation through the AV node may be very limited due to AV node refractoriness so that atrial fibrillation can be sustained indefinitely, since the ventricles continue to drive circulation, albeit inefficiently.

AF monitoring systems have been developed for use in an ambulatory setting, which may be either external, such as a Holter monitor, or internal, such as implantable cardiac monitors or "loop recorders". These systems continually sense cardiac electrical signals from a patient's heart, process the signals to detect AF and upon detection, record the electrical signals for subsequent review and analysis by a care provider.

More recently, interest has increased in providing improved implantable cardiac monitors. It has been proposed that implantable cardiac monitors may be used for diagnosis of re-current AF after surgical AF ablation, catheter AF ablation, atrial fibrillation ablation and cryptogenic stroke. Further, there is an interest in managing AF episodes in connection with medication usage, as well as monitoring AF in connection with detecting periodic atrial cardioversion.

However, existing algorithms used by monitoring systems for detecting AF are primarily based on the irregularity of R-waves, since the system uses only 2 electrodes. Due to the difficulty in detecting P-waves, these systems may provide false positives, and declare AF detection, when AF did not necessarily exist. As one example, certain AF detection algorithms may be confused when a patient exhibits irregular rhythms that are not AF episodes. Since the monitoring system does not detect P waves, when a clinician views stored electrocardiogram data, the physician needs to analyze the rhythm in an effort to observe where sinus beats or other aberrations are present.

Further, existing AF detection algorithms may experience undue false positives in connection with certain irregular rhythm patterns. Existing AF algorithms may not exhibit sufficient positive predictive value (PPV) of AF episode detection and duration (burden). Heretofore, it has been proposed to utilize "P-wave evidence", in connection with AF detection algorithms, in an effort to reduce the false positives declared by AF detection algorithms. In general, P-wave evidence related algorithms look backwards in time through an ECG signal for the presence of P-waves and discard the data when evidence of P waves is present. However, P-wave evidence-based algorithms may still exhibit false positives and may not be effective in all circumstances.

Therefore, a need remains for improved methods and systems for discriminating AF detection and reducing false detection of atrial fibrillation.

SUMMARY

In accordance with embodiments herein a computer implemented method is provided for discriminating rhythm patterns in cardiac activity. The method is under control of one or more processors configured with specific executable instructions. The method obtains cardiac activity data for multiple cardiac beats over a predetermined period of time. Multi-beat segments within the cardiac activity data exhibit different rhythm patterns of interest including fast and slow irregular rhythm patterns. The method calculates a cardiac beats timing relation representative of intervals between the cardiac beats within a measurement window. The method designates the cardiac beats timing relation to have one of the rhythm patterns of interest based on a rate threshold, identifies when successive multi-beat segments exhibit a rhythm pattern transition between the fast and slow irregular rhythm patterns, and records the rhythm patterns transition in connection with the cardiac activity data.

Optionally, the method further comprises, based on the rhythm patterns transition, declaring the cardiac activity data to exhibit a Tachy-Brady episode (an episode indicative of Tachy-Brady Syndrome) and recording information indicative of the Tachy-Brady episode in connection with the cardiac activity data. Further the method may declare the cardiac activity data to exhibit a Tachy-Brady episode when at least two rhythm patterns transitions are identified between the alternating fast and slow irregular rhythm patterns. The successive multi-beat segments may include first and second multi-beat segments. The first multi-beat segment may have one of the fast or slow rhythm patterns. The second multi-beat segment may have another of the slow or fast rhythm patterns, respectively.

Optionally, the method further comprises displaying the cardiac activity data on a display as an electrocardiogram signal over time, and displaying a Tachy-Brady episode marker at a point along the electrocardiogram signal corresponding to the rhythm patterns transition between the fast and slow rhythm patterns. The rhythm patterns transition may represent a change from a first multi-beat segment having a slow rhythm pattern to a second multi-beat segment having a fast rhythm pattern. The rhythm patterns transition may represent a change from a first multi-beat segment having a fast rhythm pattern to a second multi-beat segment having a slow rhythm pattern. The method may record a plurality of rhythm patterns transitions over time and based thereon calculating and displaying a Tachy-Brady burden associated with the cardiac activity data. The Tachy-Brady burden may represent an amount of time, during which the cardiac activity data experiences Tachy-Brady episodes.

Optionally, calculating and designating operations are repeated for a plurality of multi-beat segments within the cardiac activity data with the successive multi-beat segments partially overlap to include at least one common cardiac beat. The calculating operation may include determining an interval average for beat to beat intervals associated with the multi-beat segment. The designating operation may include comparing the cardiac beats timing relation to the rate threshold. The rate threshold may include a bradycardia threshold and a tachycardia threshold. The designating operation may include comparing the cardiac beats timing relation to at least one of the bradycardia or tachycardia thresholds in connection with designating the current cardiac beats timing relation to represent a fast, normal or slow rhythm pattern.

In accordance with embodiments herein a system is provided for discriminating rhythm patterns in cardiac activity. The system comprises at least one processor, and a memory coupled to the at least one processor. The memory stores program instruction. The program instructions are executable by the at least one processor to obtain cardiac activity data for multiple cardiac beats over a predetermined period of time, wherein multi-beat segments within the cardiac activity data exhibit different rhythm patterns of interest including fast and slow rhythm patterns. The program instructions calculate a cardiac beats timing relation representative of intervals between the cardiac beats within a measurement window, wherein the measurement window is configured to overlap the corresponding multi-beat segment and designates the cardiac beats timing relation to have one of the rhythm patterns of interest based on a rate threshold. The program instructions further identify when successive multi-beat segments exhibit a rhythm pattern transition between the fast and slow rhythm patterns and records the rhythm patterns transition in connection with the cardiac activity data.

Optionally, the system further comprises an implantable cardiac rhythm monitoring device that houses the at least one processor and memory therein. The cardiac rhythm monitoring device further comprises electrodes to sense the cardiac activity data. The memory, within the cardiac rhythm monitoring device, may comprise a Tachy-Brady tracking segment configured to store flags in connection with each of the multi-beat segments. The flags may designate the corresponding multi-beat segments to represent a fast rhythm pattern or a slow rhythm pattern. The memory may include a Tachy-Brady episode segment that may be configured to store information in connection with Tachy-Brady episodes.

Optionally, the system further comprises a sensing circuit configured to sense the cardiac activity data, at least one of electrocardiogram (EGM) data or subcutaneous electrocardiograph (ECG) data from one or more implanted or external electrodes. The processor may be configured to declare the cardiac activity data to exhibit a Tachy-Brady episode and the memory may be configured to record information indicative of the Tachy-Brady episode in connection with the cardiac activity data. The processor may be configured to calculate, from a plurality of rhythm patterns transitions occurring over time, a Tachy-Brady burden exhibited within the cardiac activity data. The system further comprising an external monitor configured to display a Tachy-Brady burden representing an amount of time, during which the cardiac activity data experienced Tachy-Brady episodes.

BRIEF DESCRIPTION OF THE DRAWINGS

FIG. 7 illustrates an example of one manner by which AF burden and Tachy-Brady daily burden information may be presented to a clinician in accordance with embodiments herein.

DETAILED DESCRIPTION

Figure 1A:
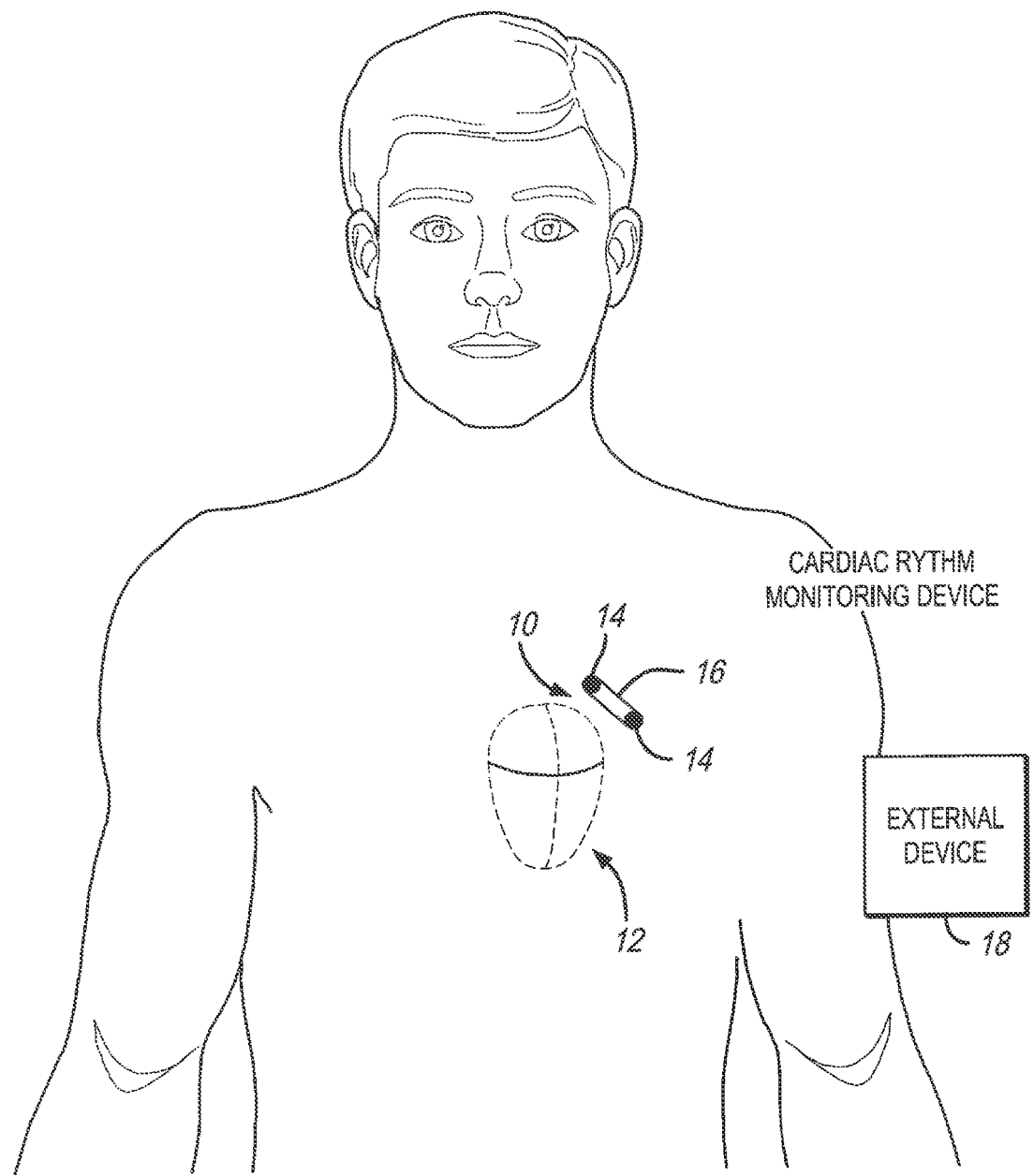
FIG. 1A illustrates an implantable cardiac monitoring (ICM) device intended for subcutaneous implantation at a site near the heart in accordance with embodiments herein.

In accordance with embodiments herein, methods and systems are described for detecting and discriminating episodes of interest, namely Tachy-Brady episodes, also referred to as fast-slow episodes (indicative of sick sinus syndrome). This abnormal heart rhythm problem is often seen in people who have been diagnosed with atrial fibrillation. The fast-slow (or Tachy-Brady) episodes are identified based on alternating rhythm patterns that change in a relatively abrupt manner (e.g., with one or a select few beats). The fast-slow (Tachy-Brady) episodes represent groups of cardiac beats exhibiting a bradycardia behavior followed or preceded by groups of cardiac beats exhibiting a tachycardia behavior. The transition between the Bradycardia and Tachycardia behavior may be detectable within a small number of beats.

In accordance with embodiments herein, methods and systems record and display to the physician electrocardiogram (EGM) data that exhibits the fast-slow characteristic. By definition, AF is "irregularly irregular" and may contain both fast AF and periods of slow conduction, or "slow AF". For example, an irregularity (e.g. potentially AF) episode may be detected whether the rhythm alternates between groups of fast ectopic beats and groups of slow ectopic beats. Embodiments herein use the AF irregularity detection method to first detect these "fast" and "slow" irregularities, and then applies further discrimination techniques to detect if the "slow beats" are perhaps true Bradycardia and not slow AF. By way of example, interval averages may be determined over a select number of beats (e.g. at least 4 beats, 8 beats or more). While slow AF can appear like Bradycardia, AF generally has single, long pauses of non-conduction, with primarily irregular, irregular Fast AF beats. The use of 4 or 8 or more beats helps to distinguish "true Brady" as in Tachy-Brady Syndrome, and is customizable by the clinician since no two patients are alike, and AF can present in many ways. In at least some embodiments, a user may selectively program limits/thresholds utilized to identify fast ectopic beats and slow ectopic beats. An ectopic beat (or cardiac ectopy) is a disturbance of the cardiac rhythm frequently related to the electrical conduction system of the heart, in which beats arise from fibers or group of fibers outside the region in the heart muscle ordinarily responsible for impulse formation (e.g., the sinoatrial node).

The fast-slow altering irregularity exhibited in certain rhythm patterns represents a unique event type, which may be referred to as a sick sinus syndrome (SSS) episode, or Tachy-Brady episode. The Tachy-Brady episodes are recorded in connection with the EGM data stream and subsequently presented to a user for review. The methods and systems also enable the user to subsequently reject or include Tachy-Brady episodes in future AF burden calculations.

Embodiments herein detect Tachy-Brady episodes based on sudden rhythm changes including alternating patterns of fast and slow rhythms. By way of example, the Tachy-Brady episode detection algorithms may be implemented in various types of external or implantable cardiac monitoring devices. The Tachy-Brady episode detection algorithms analyze a timing relation such as interval averages (e.g. a beat to beat interval between at least 4 beats, up to eight beats, or more than eight beats). The interval averages are compared with user programmable ventricular rate thresholds, such as a bradycardia threshold and a tachycardia threshold. The relation between the timing relation and the bradycardia and tachycardia thresholds are utilized to identify fast and slow rhythms, and to distinguish transitions between the fast and slow rhythms. When a fast/slow rhythm pattern repeats, embodiments herein classify the related cardiac activity as a Tachy-Brady episode. The Tachy-Brady episode is presented on a display of an external device (e.g. workstation) to a user as a unique type of episode. The user may then elect to include or exclude the Tachy-Brady episode from subsequent calculations of AF burden. For example, when a Tachy-Brady episode appears to be primarily/mostly AF, the user may elect to include the Tachy-Brady episode as part of future AF burden data collection. The user may also elect to change the Brady threshold to more accurately detect Tachy-Brady episodes distinct from a given patients AF rhythm. Alternatively, when a Tachy-Brady episode appears to be primarily not-AF, the user may elect to exclude the Tachy-Brady episode from the future AF burden data collection. Accordingly, based on program settings for the bradycardia and tachycardia thresholds, and upon inputs from a clinician, thereafter subsequent Tachy-Brady episodes will be included or excluded from the AF burden.

In accordance with at least some embodiments, the clinician may adjust the ventricular rate thresholds settings based on information presented in the EGM data. The clinician is able to see the EGM data associated with Tachy-Brady episodes, along with the corresponding mean slow ventricular rate and mean fast ventricular rate, and based thereon may further refine the program to adjust ventricular rate thresholds. By way of example, the ventricular rate threshold may represent a single threshold (e.g. between 50 and 100 beats per minute). Additionally or alternatively, the ventricular rate threshold may be comprised of two thresholds, namely a bradycardia threshold (e.g. at or less than 60 bpm) and a tachycardia threshold (at or above 90 bpm). In accordance with at least some embodiments, the Tachy-Brady episode detection algorithms herein search for alternating transitions/jumps in the average cardiac rhythm above and below the threshold(s).

FIG. 1A illustrates an implantable cardiac rhythm monitoring device (ICM) 10 intended for subcutaneous implantation at a site near the heart 12. The monitoring device includes a pair of spaced-apart sense electrodes 14 positioned with respect to a housing 16. The sense electrodes 14 provide for detection of far field electrogram signals. Numerous configurations of electrode arrangements are possible. For example, the electrodes 14 may be located on the same side of the housing 16. Alternatively, the electrodes 14 may be located on opposite sides of the housing 16. One of the electrodes 14 may be formed as part of the housing 16, for example, by coating all but a portion of the housing with a nonconductive material such that the uncoated portion forms the electrode. In this case, the other of the electrodes 14 may be electrically isolated from the housing electrode by placing it on a component separate from the housing, such as a header (not shown). In other configurations, the electrodes 14 may be located on short, stub leads extending away from the housing but coupled thereto through one or more headers so as to interface with internal components. The housing 16 includes various other components such as: sense electronics for receiving signals from the electrodes, a microprocessor for processing the signals in accordance with algorithms, such as the AF detection algorithm described herein, a loop memory for temporary storage of electrograms, a device memory for long-term storage of electrograms upon certain triggering events, such as AF detection, sensors for detecting patient activity and a battery for powering components.

The monitoring device 10 senses far field, subcutaneous electrograms, processes the electrograms to detect arrhythmias and if an arrhythmia is detected, and automatically records the electrograms in memory for subsequent transmission to an external device 18. Electrogram processing and arrhythmia detection is provided for, at least in part, by algorithms embodied in the microprocessor. In one configuration, the monitoring device is operative to detect atrial fibrillation.

The monitoring device 10 includes one or more processors and memory that stores program instructions directing the processors to implement an AF detection algorithm and an algorithm for identifying Tachy-Brady episodes in accordance with embodiments herein.

Figure 1B:
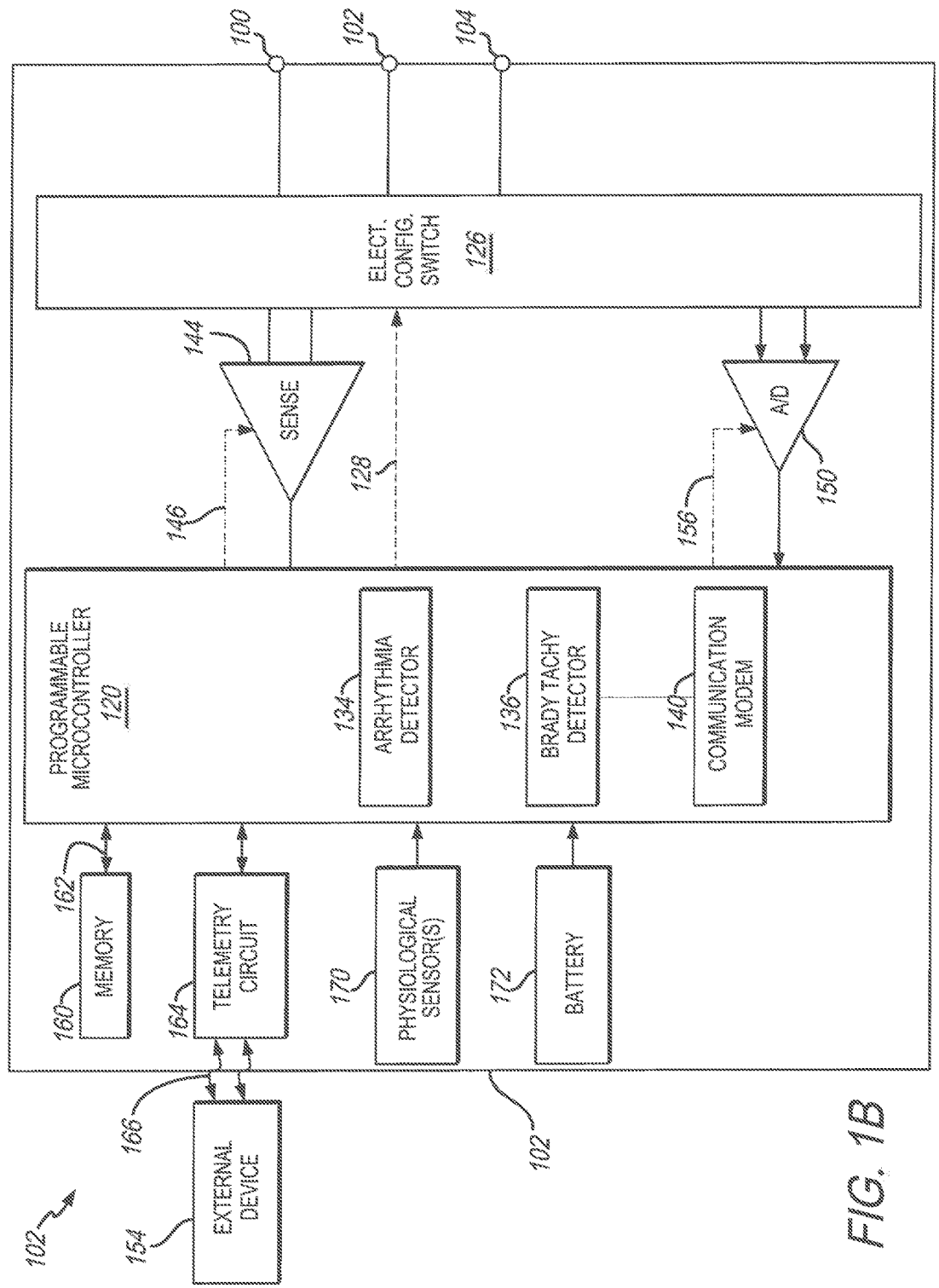
FIG. 1B shows a block diagram of an exemplary ICM device that is configured to be implanted into the patient in accordance with embodiments herein.

FIG. 1B shows a block diagram of an exemplary ICM 102 (such as device 10) that is configured to be implanted into the patient. Optionally, the ICM 102 may be provided as an external device that is worn, held or otherwise located proximate to the patient during operation. The ICM 102 may be implemented to monitor ventricular activity alone, or both ventricular and atrial activity through sensing circuitry. The ICM 102 has a housing 100 to hold the electronic/computing components. The housing 100 (which is often referred to as the "can", "case", "encasing", or "case electrode") may be programmably selected to act as an electrode for certain sensing modes. Housing 100 further includes a connector (not shown) with at least one terminal 102 and preferably a second terminal 104. The terminals 102, 104 may be coupled to sensing electrodes that are provided upon or immediately adjacent the housing 100. Optionally, more than two terminals 102, 104 may be provided in order to support more than two sensing electrodes to support a true bipolar sensing scheme using the housing as a reference electrode. Additionally or alternatively, the terminals 102, 104 may be connected to one or more leads having one or more electrodes provided thereon, where the electrodes are located in various locations about the heart. The type and location of each electrode may vary.

In at least some embodiments, the ICM 102 is configured to be placed subcutaneously utilizing a minimally invasive approach. Subcutaneous electrodes are provided on the housing 100 to simplify the implant procedure and eliminate a need for a transvenous lead system. The sensing electrodes may be located on opposite sides of the device and designed to provide robust episode detection through consistent contact at a sensor-tissue interface. The ICM 102 may be configured to be activated by the patient or automatically activated, in connection with recording subcutaneous ECG signals.

The ICM 102 includes a programmable microcontroller 120 that controls various operations of the ICM 102, including cardiac monitoring. Microcontroller 120 includes a microprocessor (or equivalent control circuitry), RAM and/or ROM memory, logic and timing circuitry, state machine circuitry, and I/O circuitry. The microcontroller 120 also performs the operations described herein in connection with collecting cardiac activity data and analyzing the cardiac activity data to identify Tachy-Brady episodes.

A switch 126 is optionally provided to allow selection of different electrode configurations under the control of the microcontroller 120. The electrode configuration switch 126 may include multiple switches for connecting the desired electrodes to the appropriate I/O circuits, thereby facilitating electrode programmability. The switch 126 is controlled by a control signal 128 from the microcontroller 120. Optionally, the switch 126 may be omitted and the I/O circuits directly connected to the housing electrode 100 and a second electrode 102. Microcontroller 120 includes an arrhythmia detector 134, and a Tachy-Brady detector 136. The arrhythmia detector 134 is configured to analyze cardiac activity data to identify potential AF episodes as well as other arrhythmias (e.g. Tachcardias, Bradycardias, Asystole, etc.). By way of example, the arrhythmia detector 134 may implement an AF detection algorithm as described in U.S. Pat. No. 8,135,456, the complete subject matter of which is incorporated herein by reference. The Tachy-Brady detector 136 is configured to analyze cardiac activity data to identify Tachy-Brady episodes as explained herein. In accordance with at least some embodiments, when a potential AF episode is detected, the Tachy-Brady detector is utilized to determine whether the episode is in fact an AF episode or instead a Tachy-Brady episode. Additionally or alternatively, the arrhythmia detector 134 and the Tachy-Brady detector 136 may separately analyze the cardiac activity data, in which case the Tachy-Brady detector 136 may analyze cardiac activity data regardless of whether potential AF episodes have been detected. Although not shown, the microcontroller 120 may further include other dedicated circuitry and/or firmware/software components that assist in monitoring various conditions of the patient's heart and managing pacing therapies.

The ICM 102 is further equipped with a communication modem (modulator/demodulator) 140 to enable wireless communication. In one implementation, the communication modem 140 uses high frequency modulation, for example using RF or Blue Tooth telemetry protocols. The signals are transmitted in a high frequency range and will travel through the body tissue in fluids without stimulating the heart or being felt by the patient. The communication modem 140 may be implemented in hardware as part of the microcontroller 120, or as software/firmware instructions programmed into and executed by the microcontroller 120. Alternatively, the modem 140 may reside separately from the microcontroller as a standalone component. The modem 140 facilitates data retrieval from a remote monitoring network. The modem 140 enables timely and accurate data transfer directly from the patient to an electronic device utilized by a physician.

The ICM 102 includes sensing circuitry 144 selectively coupled to one or more electrodes that perform sensing operations, through the switch 126 to detect cardiac activity data indicative of cardiac activity. The sensing circuitry 144 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the cardiac signal of interest. In one embodiment, switch 126 may be used to determine the sensing polarity of the cardiac signal by selectively closing the appropriate switches.

The output of the sensing circuitry 144 is connected to the microcontroller 120 which, in turn, determines when to store the cardiac activity data (digitized by the A/D data acquisition system 150) in the memory 160. For example, the microcontroller 120 may only store the cardiac activity data (from the A/D data acquisition system 150) in the memory 160 when a potential AF episode or Tachy-Brady episode is detected. The sensing circuitry 144 receives a control signal 146 from the microcontroller 120 for purposes of controlling the gain, threshold, polarization charge removal circuitry (not shown), and the timing of any blocking circuitry (not shown) coupled to the inputs of the sensing circuitry.

In the example of FIG. 1B, a single sensing circuit 144 is illustrated. Optionally, the ICM 102 may include multiple sensing circuits, similar to sensing circuit 144, where each sensing circuit is coupled to two or more electrodes and controlled by the microcontroller 120 to sense electrical activity detected at the corresponding two or more electrodes. The sensing circuit 144 may operate in a unipolar sensing configuration (e.g., housing 100 to electrode 102) or in a bipolar sensing configuration (e.g., between electrodes 102 and 104 referenced to the housing electrode 100). Optionally, the sensing circuit 144 may be removed entirely and the microcontroller 120 perform the operations described herein based upon the EGM signals from the A/D data acquisition system 150 directly coupled to the electrodes 100, 102 and/or 104.

The ICM 102 further includes an analog-to-digital A/D data acquisition system (DAS) 150 coupled to one or more electrodes via the switch 126 to sample cardiac signals across any pair of desired electrodes. The data acquisition system 150 is configured to acquire cardiac electrogram (EGM) signals, convert the raw analog data into digital data, and store the digital data for later processing and/or telemetric transmission to an external device 154 (e.g., a programmer, local transceiver, or a diagnostic system analyzer). The data acquisition system 150 is controlled by a control signal 156 from the microcontroller 120. The EGM signals are utilized as the cardiac activity data that is analyzed for potential AF episodes and Tachy-Brady episodes.

By way of example, the external device 154 may represent a bedside monitor installed in a patient's home and utilized to communicate with the ICM 102 while the patient is at home, in bed or asleep. The external device 154 may be a programmer used in the clinic to interrogate the device, retrieve data and program detection criteria and other features. The external device 154 may be a device that can be coupled over a network (e.g. the Internet) to a remote monitoring service, medical network and the like. The external device 154 facilitates access by physicians to patient data as well as permitting the physician to review real-time ECG signals while being collected by the ICM 102.

The microcontroller 120 is coupled to a memory 160 by a suitable data/address bus 162. The programmable operating parameters used by the microcontroller 120 are stored in memory 160 and used to customize the operation of the ICM 102 to suit the needs of a particular patient. Such operating parameters define, for example, detection rate thresholds, sensitivity, automatic features, arrhythmia detection criteria, activity sensing or other physiological sensors, and electrode polarity, etc.

In addition, the memory 160 stores the cardiac activity data, as well as the markers and other data content associated with detection of AF episodes and Tachy-Brady episodes. The operating parameters of the ICM 102 may be non-invasively programmed into the memory 160 through a telemetry circuit 164 in telemetric communication via communication link 166 with the external device 154. The telemetry circuit 164 allows intracardiac electrograms and status information relating to the operation of the ICM 102 (as contained in the microcontroller 120 or memory 160) to be sent to the external device 154 through the established communication link 166. In accordance with embodiments herein, the telemetry circuit 164 conveys the cardiac activity data, markers and other information related to AF episodes and Tachy-Brady episodes.

The ICM 102 may further include magnet detection circuitry (not shown), coupled to the microcontroller 120, to detect when a magnet is placed over the unit. A magnet may be used by a clinician to perform various test functions of the unit 102 and/or to signal the microcontroller 120 that the external device 154 is in place to receive or transmit data to the microcontroller 120 through the telemetry circuits 164.

The ICM 102 can further include one or more physiologic sensor 170. Such sensors are commonly referred to (in the pacemaker arts) as "rate-responsive" or "exercise" sensors. The physiological sensor 170 may further be used to detect changes in the physiological condition of the heart, or diurnal changes in activity (e.g., detecting sleep and wake states). Signals generated by the physiological sensors 170 are passed to the microcontroller 120 for analysis and optional storage in the memory 160 in connection with the cardiac activity data, markers, episode information and the like. While shown as being included within the unit 102, the physiologic sensor(s) 170 may be external to the unit 102, yet still be implanted within or carried by the patient. Examples of physiologic sensors might include sensors that, for example, activity, temperature, sense respiration rate, pH of blood, ventricular gradient, activity, position/posture, minute ventilation (MV), and so forth.

A battery 172 provides operating power to all of the components in the ICM 102. The battery 172 is capable of operating at low current drains for long periods of time. The battery 172 also desirably has a predictable discharge characteristic so that elective replacement time can be detected. As one example, the unit 102 employs lithium/silver vanadium oxide batteries. The battery 172 may afford various periods of longevity (e.g. three years or more of device monitoring). In alternate embodiments, the battery 172 could be rechargeable. See for example, U.S. Pat. No. 7,294,108, Cardiac event microrecorder and method for implanting same, which is hereby incorporated by reference.

The ICM 102 provides a simple to configure data storage option to enable physicians to prioritize data based on individual patient conditions, to capture significant events and reduce risk that unexpected events are missed. The ICM 102 may be programmable pre- and post-trigger event storage. For example, the ICM 102 may be automatically activated to store 10-60 seconds of activity data prior to an event of interest and/or to store 10-60 seconds of post event activity. Optionally, the ICM 102 may afford patient triggered activation in which pre-event activity data is stored, as well as post event activity data (e.g. pre-event storage of 1-15 minutes and post-event storage of 30-60 seconds). Optionally, the ICM 102 may afford manual (patient triggered) or automatic activation for EGM storage. Optionally, the ICM 102 may afford additional programming options (e.g. asystole duration, bradycardia rate, tachycardia rate, tachycardia cycle count). The amount of EGM storage may vary based upon the size of the memory 160.

The ICM 102 may provide comprehensive safe diagnostic data reports including a summary of heart rate, in order to assist physicians in diagnosis and treatment of patient conditions. By way of example, reports may include episodal diagnostics for auto trigger events, episode duration, episode count, episode date/time stamp and heart rate histograms. The ICM 102 may be configured to be relatively small (e.g. between 2-10 cc in volume) which may, among other things, reduce risk of infection during implant procedure, afford the use of a small incision, afford the use of a smaller subcutaneous pocket and the like. The small footprint may also reduce implant time and introduce less change in body image for patients.

Figure 1C:
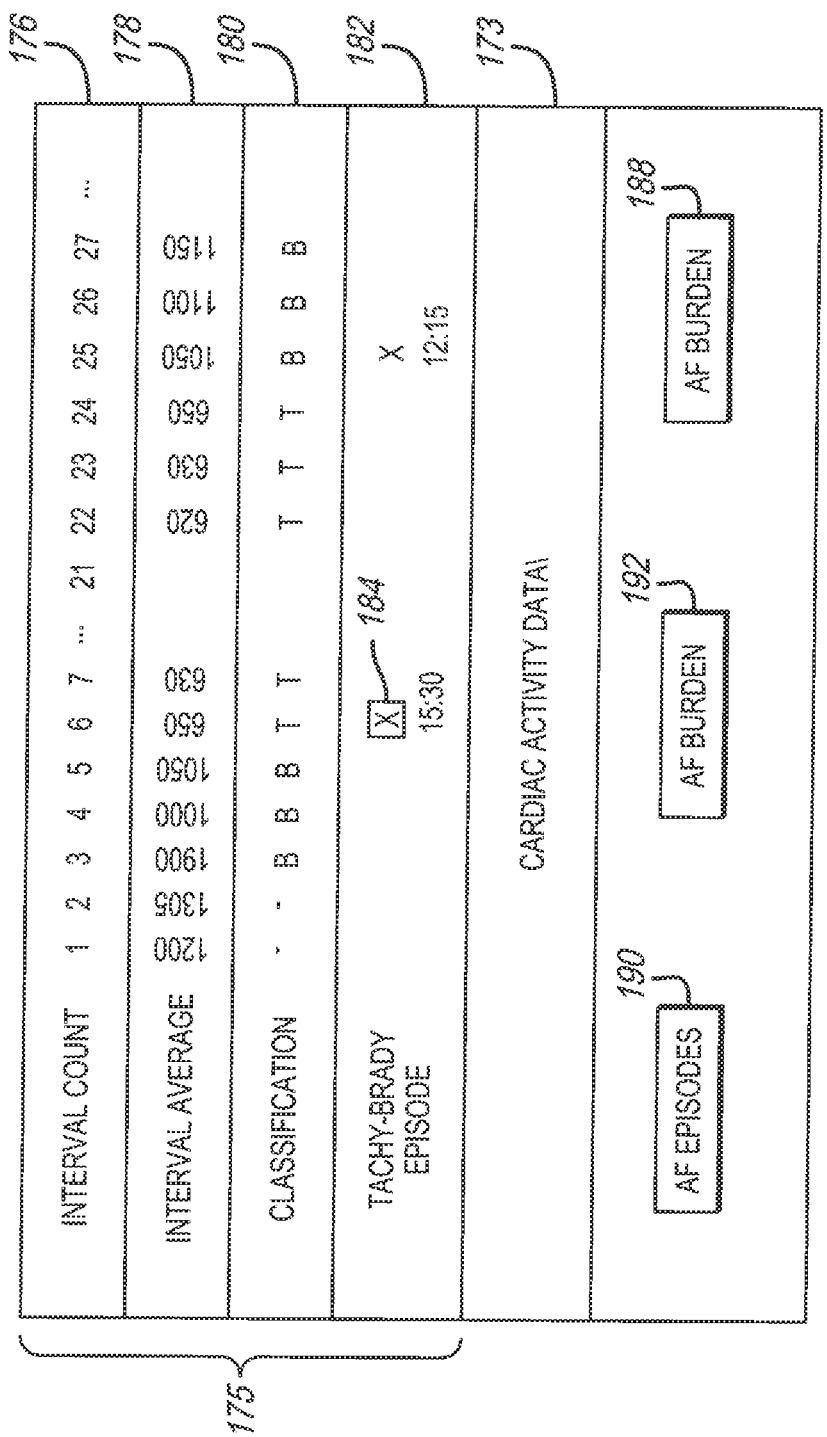
FIG. 1C illustrates a block diagram of a portion of the memory in the ICM that is utilized in accordance with an embodiment herein.
Figure 4:
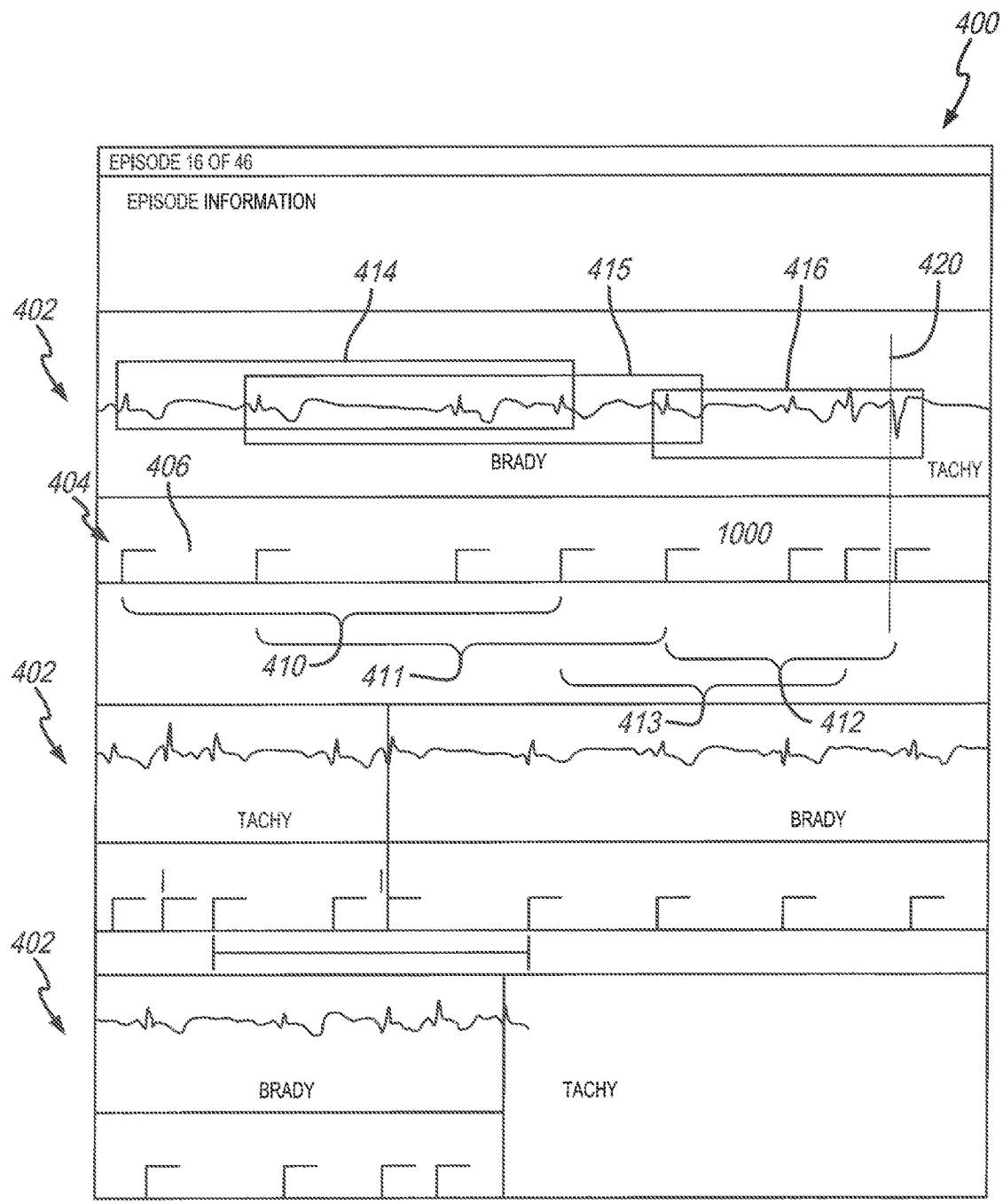
FIG. 4 illustrates an example of the cardiac activity data that may be collected by an implantable cardiac monitor for a portion of a predetermined period of time in accordance with embodiments herein.

FIG. 1C illustrates a block diagram of a portion of the memory 160 in the ICM that is utilized in accordance with an embodiment herein. The memory 160 includes a segment 173 for storing cardiac activity data. The memory 160 includes a Tachy-Brady tracking segment 175 that is utilized in connection with the operations described herein to analyze cardiac activity data and identify Tachy-Brady episodes. The segment 175 includes an interval count segment 176, within which each count corresponds to a multi-beat segment (and associated measurement window) of the cardiac activity data. As explained herein, the cardiac activity data is apportioned into successive multi-beat segments (overlapping or non-overlapping). Adjacent beats within the multi-beat segment are separated by individual beat to beat intervals, with the overall multi-beat segment having a timing relation such as an interval average. By way of example, the interval counts #2, #3 (in 176, FIG. 1C) may correspond to the multi-beat segments 410, 411 (FIG. 4). The interval counts #5 and #6 may correspond to the multi-beat segments 413 and 412 in FIG. 4, respectively.

The tracking segment 175 also includes interval averages 178 that are recorded in connection with each multi-beat segment. The interval average 178 represents one type of cardiac beat timing relation. Optionally, the interval average 178 may be replaced with or supplemented with other information representative of the cardiac beat timing relation. The interval count #1 includes an interval average of 1200 ms, the interval count #6 includes an interval average of 650 ms.

The tracking segment 175 also includes an interval classification flag segment 180 that stores classification flags in connection with each count interval. In the example of FIG. 1C, the interval classification flag segment 180 includes a bradycardia flag "B" in connection with each of interval counts #3-#5 and #25-#27. The interval classification flag segment 180 includes a tachycardia flag "T" in connection with each of interval counts #6-#7 and #22-#24. The segment 180 also includes dashed lines "-", that may be recorded in connection with multi-beat segments that do not exhibit either a bradycardia or tachycardia rhythm pattern (e.g. when indicating a normal rhythm pattern or when the rhythm pattern is indeterminate).

The tracking segment 175 includes a Tachy-Brady episode segment 182 that records information in connection with individual Tachy-Brady episodes. For example, the segment 182 may record markers 184 aligned with cardiac beats that are associated with a rhythm pattern transition between Brady and Tachy rhythm patterns or vice versa. While the clinical name used through is "Tachy-Brady Syndrome", the detection methods and systems described herein detect transitions from Brady to Tachy and from Tachy to Brady, and both detections are within the spirit of "Tachy-Brady Syndrome detection" as described herein. The segment 182 also records other information concerning Tachy-Brady episodes, such as the episode duration 186, time of day at which the Tachy-Brady episode occurred and the like. Optionally, the tracking segment 175 may record additional information regarding a Tachy-Brady episode, such as a condition or state of the patient (e.g. whether the patient is active at the time of the event, asleep, standing, in a prone position and the like).

The memory 160 may also store Tachy-Brady burden information 188. For example, the Tachy-Brady burden information 188 may include the information illustrated in FIGS. 7 and 8. The memory 160 may also store AF episodes 190 and AF burden related information 192.

Figure 2:
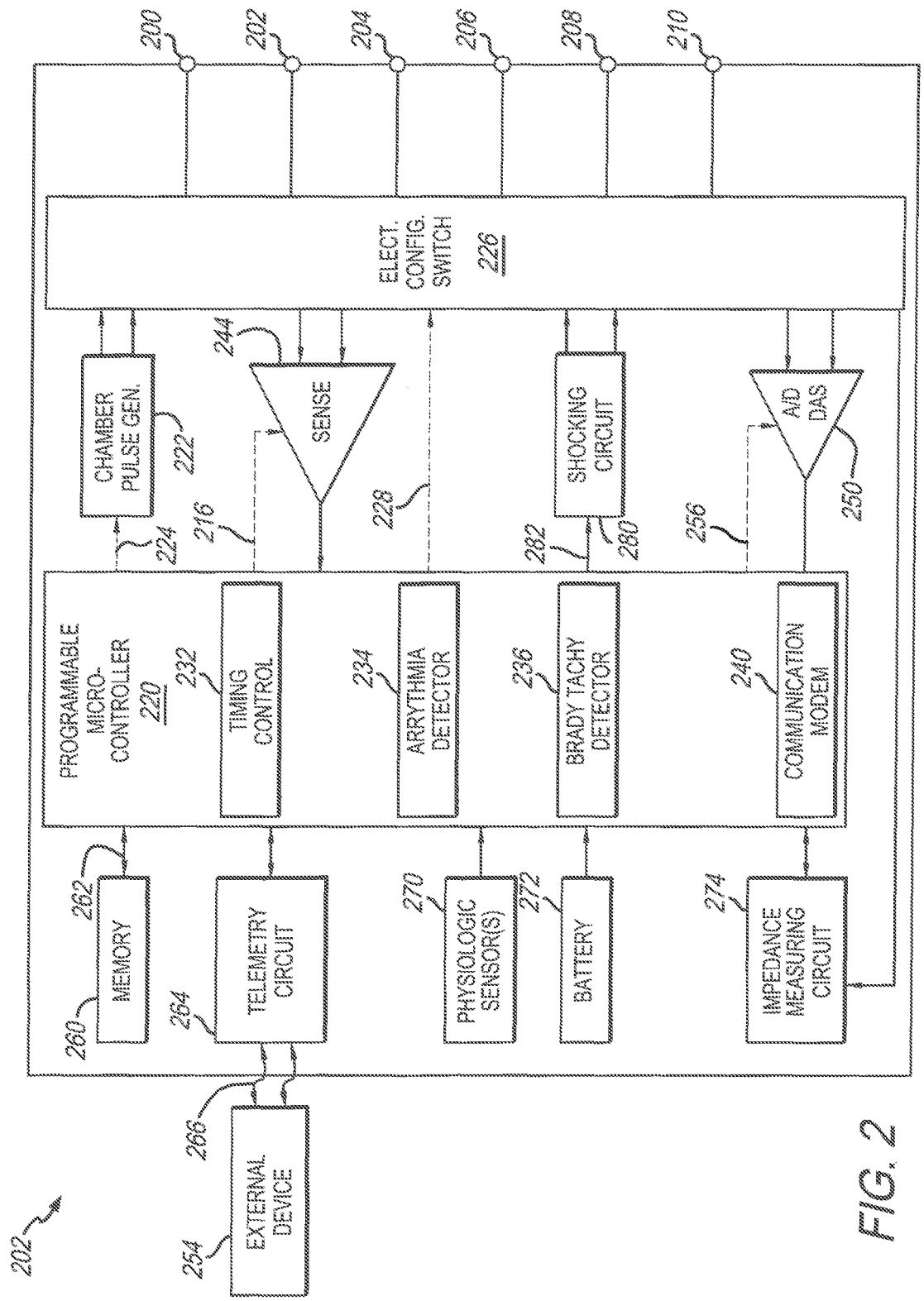
FIG. 2 shows an exemplary ICM that is configured to be implanted into the patient as part of an implantable cardiac system in accordance with embodiments herein.

FIG. 2 shows an exemplary Tachy-Brady detector that is configured to be implanted into the patient as part of an implantable stimulation device 202, either a cardiac pacemaker or ICD system. The implantable device 202 may be implemented as a full-function biventricular pacemaker, equipped with both atrial and ventricular sensing and pacing circuitry for four chamber sensing and stimulation therapy (including both pacing and shock treatment). Optionally, the implantable device 202 may provide full-function cardiac resynchronization therapy. Alternatively, the implantable device 202 may be implemented with a reduced set of functions and components. For instance, the implantable device may be implemented without ventricular sensing and pacing.

The implantable device 202 has a housing 200 to hold the electronic/computing components. The housing 200 (which is often referred to as the "can", "case", "encasing", or "case electrode") may be programmably selected to act as the return electrode for certain stimulus modes. Housing 200 further includes a connector (not shown) with a plurality of terminals 201, 204, 206, 208, and 210. The terminals may be connected to electrodes that are located in various locations within and about the heart. For example, the terminals may include: a terminal 201 to be coupled to an first electrode (e.g. a tip electrode) located in a first chamber; a terminal 204 to be coupled to a second electrode (e.g., tip electrode) located in a second chamber; a terminal 206 to be coupled to an electrode (e.g. ring) located in the first chamber; a terminal 208 to he coupled to an electrode located (e.g. ring electrode) in the second chamber; and a terminal 210 to be coupled to an electrode (e.g., coil) located in the SVC. The type and location of each electrode may vary. For example, the electrodes may include various combinations of ring, tip, coil and shocking electrodes and the like.

The implantable device 202 includes a programmable microcontroller 220 that controls various operations of the implantable device 202, including cardiac monitoring and stimulation therapy. Microcontroller 220 includes a microprocessor (or equivalent control circuitry), RAM and/or ROM memory, logic and timing circuitry, state machine circuitry, and I/O circuitry. The microcontroller 220 also performs the operations described herein in connection with collecting cardiac activity data and analyzing the cardiac activity data to identify Tachy-Brady episodes.

The implantable device 202 further includes a first chamber pulse generator 222 that generates stimulation pulses for delivery by one or more electrodes coupled thereto. The pulse generator 222 is controlled by the microcontroller 220 via control signal 224. The pulse generator 222 is coupled to the select electrode(s) via an electrode configuration switch 226, which includes multiple switches for connecting the desired electrodes to the appropriate I/O circuits, thereby facilitating electrode programmability. The switch 226 is controlled by a control signal 228 from the microcontroller 220.

In the example of FIG. 2, a single pulse generator 222 is illustrated. Optionally, the implantable device 202 may include multiple pulse generators, similar to pulse generator 222, where each pulse generator is coupled to one or more electrodes and controlled by the microcontroller 220 to deliver select stimulus pulse(s) to the corresponding one or more electrodes.

Microcontroller 220 is illustrated as including timing control circuitry 232 to control the timing of the stimulation pulses (e.g., pacing rate, atrio-ventricular (AV) delay, atrial interconduction (A-A) delay, or ventricular interconduction (V-V) delay, etc.). The timing control circuitry 232 may also be used for the timing of refractory periods, blanking intervals, noise detection windows, evoked response windows, alert intervals, marker channel timing, and so on. Microcontroller 220 also has an arrhythmia detector 234 for detecting arrhythmia conditions and a Tachy-Brady detector 236. Although not shown, the microcontroller 220 may further include other dedicated circuitry and/or firmware/ software components that assist in monitoring various conditions of the patient's heart and managing pacing therapies.

The implantable device 202 is further equipped with a communication modem (modulator/demodulator) 240 to enable wireless communication with the remote slave pacing unit 206. In one implementation, the communication modem 240 uses high frequency modulation. As one example, the modem 240 transmits signals between a pair of electrodes of the lead assembly 204, such as between the can 200 and the right ventricular tip electrode 222. The signals are transmitted in a high frequency range of approximately 20-80 kHz, as such signals travel through the body tissue in fluids without stimulating the heart or being felt by the patient.

The communication modem 240 may be implemented in hardware as part of the microcontroller 220, or as software/firmware instructions programmed into and executed by the microcontroller 220. Alternatively, the modem 240 may reside separately from the microcontroller as a standalone component.

The implantable device 202 includes sensing circuitry 244 selectively coupled to one or more electrodes that perform sensing operations, through the switch 226 to detect the presence of cardiac activity in the right chambers of the heart. The sensing circuitry 244 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the cardiac signal of interest. The automatic gain control enables the unit 202 to sense low amplitude signal characteristics of atrial fibrillation. Switch 226 determines the sensing polarity of the cardiac signal by selectively closing the appropriate switches. In this way, the clinician may program the sensing polarity independent of the stimulation polarity.

The output of the sensing circuitry 244 is connected to the microcontroller 220 which, in turn, triggers or inhibits the pulse generator 222 in response to the absence or presence of cardiac activity. The sensing circuitry 244 receives a control signal from the microcontroller 220 for purposes of controlling the gain, threshold, polarization charge removal circuitry (not shown), and the timing of any blocking circuitry (not shown) coupled to the inputs of the sensing circuitry.

In the example of FIG. 2A, a single sensing circuit 244 is illustrated. Optionally, the implantable device 202 may include multiple sensing circuits, similar to sensing circuit 244, where each sensing circuit is coupled to one or more electrodes and controlled by the microcontroller 220 to sense electrical activity detected at the corresponding one or more electrodes. The sensing circuit 244 may operate in a unipolar sensing configuration or in a bipolar sensing configuration.

The implantable device 202 further includes an analog-to-digital (A/D) data acquisition system (DAS) 250 coupled to one or more electrodes via the switch 226 to sample cardiac signals across any pair of desired electrodes. The data acquisition system 250 is configured to acquire electrogram (EGM) signals, convert the raw analog data into digital data, and store the digital data for later processing and/or telemetric transmission to an external device 254 (e.g., a programmer, local transceiver, or a diagnostic system analyzer). The data acquisition system 250 is controlled by a control signal 256 from the microcontroller 220. The EGM signals are utilized as the cardiac activity data that is analyzed for potential AF episodes and Tachy-Brady episodes.

The microcontroller 220 is coupled to a memory 260 by a suitable data/address bus 262. The programmable operating parameters used by the microcontroller 220 are stored in memory 260 and used to customize the operation of the implantable device 202 to suit the needs of a particular patient. Such operating parameters define, for example, pacing pulse amplitude, pulse duration, electrode polarity, rate, sensitivity, automatic features, arrhythmia detection criteria, and the amplitude, wave shape and vector of each shocking pulse to be delivered to the patient's heart 208 within each respective tier of therapy.

In addition, the memory 260 stores the cardiac activity data, as well as the markers and other data content associated with detection of AF episodes and Tachy-Brady episodes. The operating parameters of the implantable device 202 may be non-invasively programmed into the memory 260 through a telemetry circuit 264 in telemetric communication via communication link 266 with the external device 254. The telemetry circuit 264 allows intracardiac electrograms and status information relating to the operation of the implantable device 202 (as contained in the microcontroller 220 or memory 260) to be sent to the external device 254 through the established communication link 266. In accordance with embodiments herein, the telemetry circuit 264 conveys the cardiac activity data, markers and other information related to AF episodes and Tachy-Brady episodes.

The implantable device 202 can further include magnet detection circuitry (not shown), coupled to the microcontroller 220, to detect when a magnet is placed over the unit. A magnet may be used by a clinician to perform various test functions of the unit 202 and/or to signal the microcontroller 220 that the external programmer 254 is in place to receive or transmit data to the microcontroller 220 through the telemetry circuits 264.

The implantable device 202 can further include one or more physiologic sensors 270. Such sensors are commonly referred to as "rate-responsive" sensors because they are typically used to adjust pacing stimulation rates according to the exercise state of the patient. However, the physiological sensor 270 may further be used to detect changes in cardiac output, changes in the physiological condition of the heart, or diurnal changes in activity (e.g., detecting sleep and wake states). Signals generated by the physiological sensors 270 are passed to the microcontroller 220 for analysis. The microcontroller 220 responds by adjusting the various pacing parameters (such as rate, AV Delay, V-V Delay, etc.) at which the atrial and ventricular pacing pulses are administered. While shown as being included within the unit 202, the physiologic sensor(s) 270 may be external to the unit 202, yet still be implanted within or carried by the patient. Examples of physiologic sensors might include sensors that, for example, sense respiration rate, pH of blood, ventricular gradient, activity, position/posture, minute ventilation (MV), and so forth.

A battery 272 provides operating power to all of the components in the implantable device 202. The battery 272 is capable of operating at low current drains for long periods of time, and is capable of providing high-current pulses (for capacitor charging) when the patient requires a shock pulse (e.g., in excess of 2 A, at voltages above 2 V, for periods of 10 seconds or more). The battery 272 also desirably has a predictable discharge characteristic so that elective replacement time can be detected. As one example, the unit 202 employs lithium/silver vanadium oxide batteries.

The implantable device 202 further includes an impedance measuring circuit 274, which can be used for many things, including: lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves; and so forth. The impedance measuring circuit 274 is coupled to the switch 226 so that any desired electrode may be used.

The implantable device 202 can be operated as an implantable cardioverter/defibrillator (ICD) device, which detects the occurrence of an arrhythmia and automatically applies an appropriate electrical shock therapy to the heart aimed at terminating the detected arrhythmia. To this end, the microcontroller 220 further controls a shocking circuit 280 by way of a control signal 282. The shocking circuit 280 generates shocking pulses of low (e.g., up to 0.5 joules), moderate (e.g., 0.5-10 joules), or high energy (e.g., 21 to 40 joules), as controlled by the microcontroller 220. Such shocking pulses are applied to the patient's heart 208 through shocking electrodes. It is noted that the shock therapy circuitry is optional and may not be implemented in the ICM, as the various slave pacing units described below will typically not be configured to deliver high voltage shock pulses. On the other hand, it should be recognized that the slave pacing unit can be used within a system that includes backup shock capabilities, and hence such shock therapy circuitry may be included in the implantable device.

Next, various processes are described in connection with embodiments herein that are performed by one or more of the circuits, processors and other structures illustrated in the figures and described in the specification.

Figure 3A:
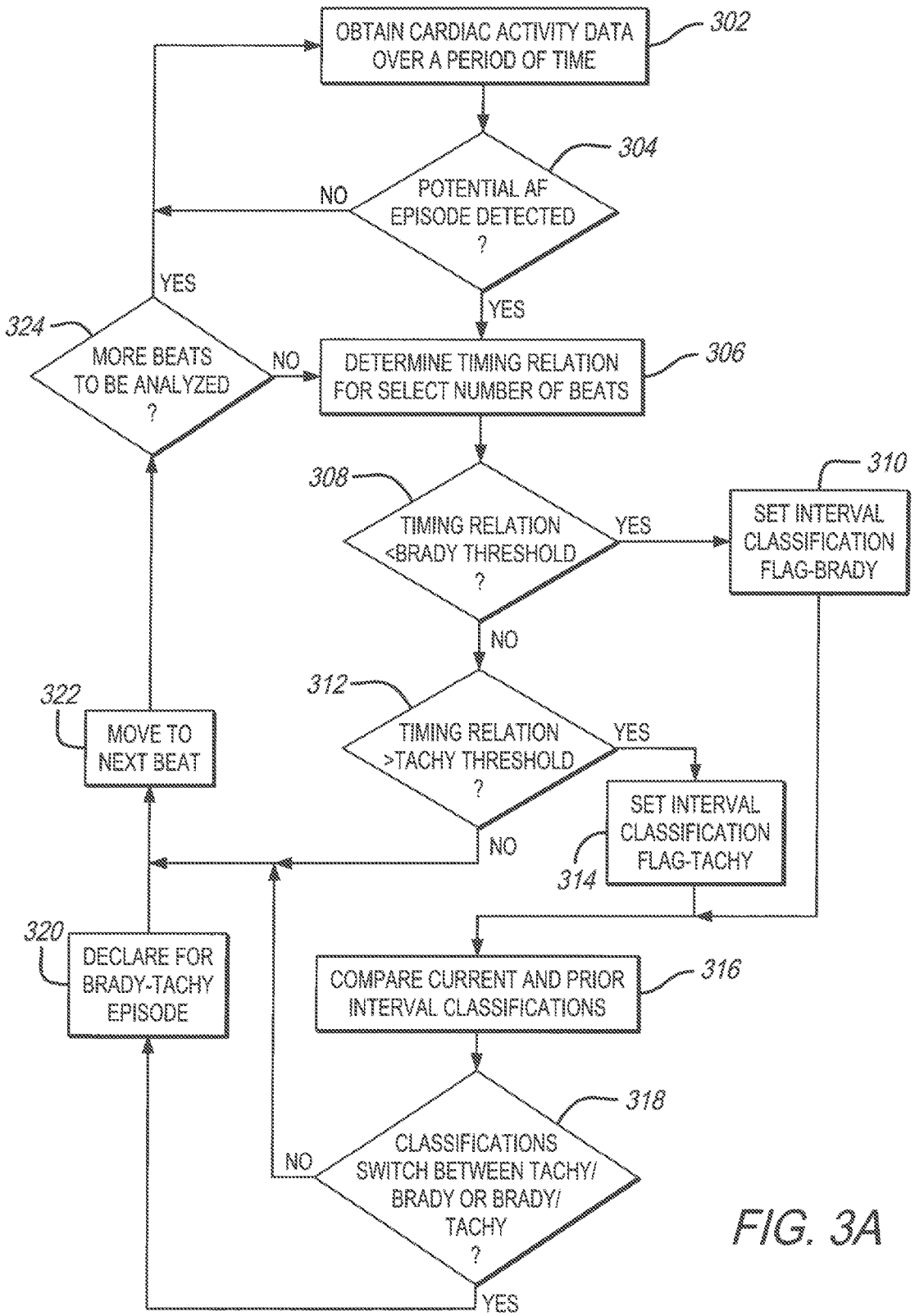
FIG. 3A illustrates a computer implemented process for discriminating rhythm patterns of interest in cardiac activity in accordance with embodiments herein.

FIG. 3A illustrates a computer implemented process for discriminating rhythm patterns of interest in cardiac activity in accordance with embodiments herein. By way of example, the operations of FIG. 3A may be implemented when cardiac activity data has been analyzed by an AF detection module (e.g. arrhythmia detector 134 in FIG. 1B) and a potential AF episode has been identified. For example, AF detection may be implemented in accordance with the process described in U.S. Pat. No. 8,135,456. When one or more potential AF episodes are identified, the process may initiate the operations of FIG. 3A in an attempt to verify whether the episode is in fact an AF episode or is a Tachy-Brady episode. Optionally, the operations of FIG. 3A may be implemented independent of whether potential AF episodes have been identified in a current cardiac activity data set.

At 302, one or more processors obtain cardiac activity data for multiple cardiac beats over a predetermined period of time. For example, the cardiac activity data may be obtained by an external or implantable monitoring device that includes electrodes that sense electrocardiogram (ECG or EGM) signals and/or intra-electrocardiogram (EGM) signals. Additionally or alternatively, the ECG and/or EGM signals may be collected by an implantable medical device (e.g. pacemaker, cardioverter defibrillator, cardiac rhythm management device, etc.). Additionally or alternatively, the cardiac activity data may have been previously acquired and stored in memory of an implantable or external monitoring device, implantable or external therapy delivery device, programmer, workstation, healthcare network or other system. When the cardiac activity data has been previously acquired, the operation at 302 represents the access and reading of the previously stored cardiac activity data.

The predetermined period of time may be programmed by a clinician, or automatically updated by one or more processors throughout operation. By way of example, the predetermined period of time may correspond to one minute, 30 minutes, one hour or otherwise.

The operations of FIG. 3A may be repeated periodically or in response to detection of particular criteria, such as detection of potential atrial fibrillation episodes or otherwise. As one example, the cardiac activity data may be collected for a one minute interval, during which multiple successive cardiac beats occur.

FIG. 4 illustrates an example of the cardiac activity data that may be collected by an implantable cardiac monitor for a portion of a predetermined period of time. FIG. 4 illustrates an example of a display 400 that presents cardiac activity data 402, as well as related markers and other content that are presented to a clinician on a display of a programmer, workstation, smart phone, tablet device, laptop computer, desktop computer or other electronic device. The cardiac activity data 402 is displayed relative to a timeline over approximately 24 seconds. The timeline may be presented in various manners, such as one continuous strip or separated into sections that are displayed proximate to one another, such as presented in three consecutive 8 second sections (e.g., 1-8 seconds, 9-16 seconds and 17-24 seconds). The cardiac activity data 402 correspond to ventricular activity sensed by the implantable cardiac monitor, and are annotated with ventricular sensing (VS) markers 404 indicating a time at which ventricular events were detected. A beat to beat interval 406 is presented to illustrate the time interval between successive VS markers 404. By way of example only, the beat to beat interval 406 between the first and second VS markers is approximately 1193 ms, while the next beat to beat interval is 1773 ms. The following beat to beat intervals are 914 ms, 965 ms, and 1141 ms.

As explained herein, sets or groups of successive cardiac beats are analyzed as multi-beat segments within the cardiac activity data. In FIG. 4, brackets are used to identify different multi-beat segments 410-412. The multi-beat segments 410 and 411 overlap and include at least one common cardiac beat. In the example of FIG. 4, the multi-beat segments 410, 411 include three common cardiac beats. Optionally, the multi-beat segments may be defined to overlap by a different amount, such as a single cardiac beat or another select number of cardiac beats. Alternatively, the multi-beat segments may be defined in a non-overlapping manner such that each multi-beat segment includes a separate and distinct group of cardiac beats. A length of the multi-beat segment 410-412 is determined by a measurement window (as conceptually illustrated by the windows 414-416) that is used herein to collect cardiac beats timing relations of interest that characterize the interrelation of the cardiac beats within the corresponding multi-beat segments. For example, the measurement windows 414-416 may be defined to include a set/group of 4, 8 or another number of individual cardiac beats that collectively defined a single multi-beat segment.

The multi-beat segments 410-412 within the cardiac activity data exhibit a corresponding rhythm pattern. Different types of rhythm patterns may be defined in various manners. By way of example, types of rhythm patterns may be characterized as "slow", "fast", "normal" or otherwise. A slow rhythm pattern represents a series of cardiac beats having an undesirably long beat to beat interval, while a fast rhythm pattern represents a series of cardiac beats having an undesirably short beat to beat interval. The rhythm patterns may be defined in various manners, such as based on the beat to beat interval, the overall duration of the multi-beat segment or otherwise. Additionally or alternatively, the rhythm pattern may be defined based on other characteristics of the cardiac activity data, such as the morphology the beats, peak amplitudes, number of changes in direction in the beat and the like.

Returning to FIG. 3A, at 304, one or more processors analyzes the cardiac activity data to determine whether a potential AF episode has been detected. When no potential AF episode is detected, the cardiac activity data need not be further analyzed for abnormal rhythm patterns. Thus, flow returns to 302 at which additional cardiac activity data is obtained. At 304, when a potential AF episode is detected, flow advances to 306. The operations at 306-324 iteratively step through the cardiac beats to analyze multi-beat segments relative to one another in connection with identifying rhythm pattern transitions of interest.

At 306, a processor calculates a cardiac beats timing relation representative of intervals between the cardiac beats within the current measurement window. As noted in connection with FIG. 4, the measurement window is configured to overlap a current multi-beat segment. With reference to FIG. 4, at 306, a cardiac beats timing relation is calculated in connection with the measurement window 415 corresponding to multi-beat segment 411. The cardiac beats timing relation may represent an interval average of the beat to beat intervals 406 between each of the cardiac beats 404 within the multi-beat segment 411. For example, the beat to beat intervals within the multi-beat segment 411 are 1773 ms, 914 ms and 965 ms, which yield an average of approximately 1217 ms. Alternatively, the cardiac beats timing relation may represent the overall duration of the multi-beat segment 411. Alternatively, the cardiac beats timing relation may correspond to another characteristic related to the intervals between the cardiac beats.

Returning to FIG. 3A, at 308, the processor compares the cardiac beats timing relation to a bradycardia threshold. The bradycardia threshold may be programmed by a clinician or automatically determined and adjusted by the monitoring device throughout operation. By way of example, the bradycardia threshold may represent a Brady ventricular rate threshold corresponding to an upper beat per minute limit, below which a patient is considered to be exhibiting a bradycardia arrhythmia. For example, the bradycardia threshold may be set at 60 or fewer beats per minute. When a multi-beat segment exhibits an interval average for the beat to beat interval below 60 bpm, the corresponding rhythm pattern is considered to represent a slow or Brady rhythm pattern. At 308, when the cardiac beats timing relation is below the Brady threshold, flow moves to 310. Otherwise, flow advances to 312. In the example of FIG. 4, the cardiac beats timing relation (e.g. interval average) corresponding to the measurement window 415 and multi-beat segment 411 is approximately 1217 ms which corresponds to approximately 49 bpm. Accordingly, when the bradycardia threshold is set at 60 bpm, flow advances to 310 as the rhythm pattern is considered slow.

At 310, the processor sets an interval classification characterizing the multi-beat segment as slow or Brady. By way of example, an interval classification flag (e.g., in segment 180 in FIG. 1C) may be set in connection with the corresponding multi-beat segment, where the flag designates a Brady/slow rhythm pattern. Optionally, alternative mechanisms may be utilized for tracking the classification of the current multi-beat segment.

Returning to 308, when flow advances to 312, the processor compares the cardiac beats timing relation to a tachycardia threshold. The tachycardia threshold may be programmed by a clinician or automatically determined and adjusted by the monitoring device throughout operation. By way of example, the tachycardia threshold may represent a Tachy ventricular rate threshold corresponding to a lower beat per minute limit, above which a patient is considered to be exhibiting a tachycardia arrhythmia. For example, the tachycardia threshold may be set at 90 or more beats per minute. When a multi-beat segment exhibits an interval average for the beat to beat interval above 90 bpm, the corresponding rhythm pattern is considered to represent a fast or Tachy rhythm pattern. At 308, when the cardiac beats timing relation is above the Tachy threshold, flow moves to 314. Otherwise, flow advances to 322 and the process moves to the next multi-beat segment. At 312, when the cardiac beats timing relation is below the Tachy threshold, the rhythm pattern may be normal or abnormal, but the rhythm pattern does not correspond to one of the fast or slow rhythm patterns of interest. Accordingly, no Tachy or Brady interval classification flag is set in connection there with.

In the example of FIG. 4, the cardiac beats timing relation, corresponding to the measurement window 416 and multi-beat segment 412, is approximately 636 ms (corresponding to the average of 1000 ms+480 ms+430 ms). An interval average of 636 ms corresponds to a heart rate of approximately 94 bpm. Accordingly, when analyzing multi-beat segment 412 with the tachycardia threshold set at 90 bpm, flow would advance to 314 as the rhythm pattern would be considered fast.

At 314, the processor sets an interval classification characterizing the multi-beat segment as fast or Tachy. By way of example, an interval classification flag (e.g., "T" in segment 180 in FIG. 1C) may be set in connection with the corresponding multi-beat segment, where the flag designates a Tachy/fast rhythm pattern. The operations at 310 and 314 designate the cardiac beats timing relation to have one of the rhythm patterns of interest based on corresponding rate thresholds (e.g. the bradycardia threshold and tachycardia threshold).

Optionally, the operations at 308-314 may be reversed such that the comparison with the tachycardia threshold and setting a Tachy interval classification flag may be performed before the comparison with the bradycardia threshold and setting a bradycardia interval classification flag. As a further option, the operations at 308-314 may be consolidated such that a single rate threshold is utilized (see FIG. 5). When the cardiac beats timing relation is above the single rate threshold, a Tachy interval classification flag is set. When the cardiac beats timing relation is below the single rate threshold, a Brady interval classification flag is set.

Following the operations at 310 or 314, flow advances to 316. At 316 and 313, the processor identifies when successive multi-beat segments exhibit a rhythm pattern (rhythm patterns) transition between fast and slow rhythm patterns. At 316, the processor compares interval classifications (e.g. flags) that were set in connection with current and prior multi-beat segments. With reference to FIG. 4, when segment 411 represents the current multi-beat segment, the operation at 316 may compare the interval classification flag set in connection with multi-beat segment 411 with the interval classification flag set in connection with the prior multi-beat segment 410. In the example of FIG. 4, multi-beat segments 410 and 411 both exhibit slow rhythm patterns.

As another example, when the current multi-beat segment corresponds to segment 412, the comparison at 316 would determine that the interval classification flag corresponding to segment 412 indicates a fast rhythm pattern, while the interval classification flag corresponding to the prior multi-beat segment 413 corresponds to a slow rhythm pattern.

At 318, the processor determines whether the interval classification, corresponding to the current and prior multi-beat segments, differ from one another and represent a change between fast and slow rhythm patterns. For example, with respect to FIG. 1C, the processor may compare the interval classification flags. In the example of FIG. 1C, and rhythm patterns transition would be identified to occur between the multi-beat segment corresponding to interval count #5 and #6. Another rhythm patterns transition would be identified to occur between the multi-beat segments corresponding to interval counts #24 and #25. When the interval classification changes, flow branches to 320. When the interval classification does not change, flow branches to 322. The operation at 318 may not necessarily distinguish between, or dependent upon, whether the order of the transition, namely whether the transition is from a fast to a slow rhythm pattern, for vice versa. For example, the operation at 318 may branch to 322 when the prior multi-beat segment exhibits a slow rhythm pattern and the current multi-beat segment exhibits a fast rhythm pattern. The operation at 318 may also branch to 322 when the prior multi-beat segment exhibits a fast rhythm pattern and the current multi-beat segment exhibits a slow rhythm pattern. In general, the operations at 318 analyze successive multi-beat segments such as first and second multi-beat segments, where the first multi-beat segment has one of a fast or slow rhythm pattern and the second multi-beat segment has another of the fast or slow rhythm pattern.

At 320, the processor declares the cardiac activity data to exhibit a Tachy-Brady episode and records information indicative of the Tachy-Brady episode in connection with the cardiac activity data. For example, at 320, the processor records/saves in memory the rhythm patterns transition in connection with the cardiac activity data. For example, the processor may record a marker in connection with the cardiac activity data indicating a Tachy-Brady episode has occurred. The marker may also indicate the point at which the rhythm pattern transition between fast and slow rhythm patterns. With reference to FIG. 4, the processor may record in memory a marker 420 that substantially aligns with the final beat in the current multi-beat segment 412, for which the rhythm patterns transition occurred. Optionally, the marker 420 may be provided in another location, such as in connection with a different beat within the multi-beat segment 412, or elsewhere.

In the foregoing example, and rhythm patterns transition is identified between successive multi-beat segments where the transition may arise following a single beat sufficient to affect the overall cardiac beats timing relation. Multi-beat segments are used to improve confidence level that the rhythm is truly Tachy-Brady Syndrome, and not just a single pause in the AF episode due to conduction block. Optionally, and rhythm patterns transition may be identified when the last distinct change occurs in the rhythm pattern. For example, one or more multi-beat segments, or a programmable number of beats, may have slow rhythm patterns, followed by one or more multi-beat segments, or a programmable number that have normal rhythm patterns, followed by one or more multi-beat segments that have fast rhythm patterns. In this alternative example, a slow rhythm pattern and a fast rhythm pattern are separated by a normal rhythm pattern. Alternatively, multi-beat segments having slow and fast rhythm patterns may be separated by one or a small number of multi-beat segments having an indeterminate rhythm pattern.

Optionally, at 320, the nature of the rhythm patterns transition may also be saved in memory as additional information. For example, when the rhythm patterns transition exhibits a change from a prior slow rhythm pattern to a current fast rhythm pattern, a corresponding slow-fast rhythm patterns transition may be recorded. When the rhythm patterns transition exhibits a change from a prior fast rhythm pattern to a current slow rhythm pattern, a corresponding fast-slow rhythm patterns transition may be recorded.

Optionally, the processor may declare a Tachy-Brady episode based upon various combinations of rhythm patterns transitions. For example, a Tachy-Brady episode may be declared when at least two rhythm patterns transitions are identified between fast and slow rhythm patterns. Optionally, the processor may record a confidence level associated with Tachy-Brady episodes. For example, when the processor declares a Tachy-Brady episode, the processor may also append a confidence percentage or other indicator representative of a likelihood that the particular episode is in fact a Tachy-Brady episode. As one example, a confidence level that a particular episode is a Tachy-Brady episode may be based in part on the abruptness, and difference in rate, of the change between fast and slow rhythm patterns. For example, when a fast or slow rhythm pattern is followed by one or more normal or indeterminate rhythm patterns that are subsequently followed by a fast or slow rhythm pattern, this combination may be characterized to have medium or low confidence that the episode is in fact a Tachy-Brady episode. Alternatively, when a fast or slow rhythm pattern is immediately followed by an opposite fast or slow rhythm pattern, a high level of confidence may be assigned that the episode is a Tachy-Brady episode. As another example, the difference in rate may be utilized as a factor in assigning a confidence to the episode. For example, when a first multi-beat segment exhibits a very slow heart rate (e.g. less than 40 bpm) while a next successive multi-beat segment exhibits a very high heart rate (e.g. greater than 100 bpm), the difference in rate associated with the rhythm patterns transition is very high (e.g. 100–40 equal 60 bpm). When the rhythm patterns transition corresponds to a large change in rate (e.g. 10, 20 or more beats per minute) in a very short period of time (e.g. one or two beats), such an indicator may afford a high level of confidence that the episode is a Tachy-Brady episode.

At 322, the processor steps to the next cardiac beat. At 324, the processor determines whether any additional cardiac beats remain to be analyzed in connection with the present set of cardiac activity data. When additional cardiac beats remain to be analyzed, flow moves from 324 to 306 and the above-described process is repeated for the next multi-beat segment. Otherwise, flow returns to 302 and a new cardiac activity data set is obtained.

After analysis of the cardiac activity data, the cardiac activity data is displayed on a display or in a report (e.g. FIG. 4) as an electrocardiogram signal over time. One or more Tachy-Brady episode markers are displayed at a point along the electrocardiogram signal corresponding to the rhythm patterns transition point between the fast and slow rhythm points. The physician may include or exclude Tachy-Brady episodes in further AF and/or Tachy-Brady burden calculation. The physician may also customize the thresholds (e.g. Tachy rate threshold, Tachy number of beats, Brady Rate Threshold, Brady number of beats) to ensure accurate detection of Tachy-Brady Episodes.

Figure 3B:
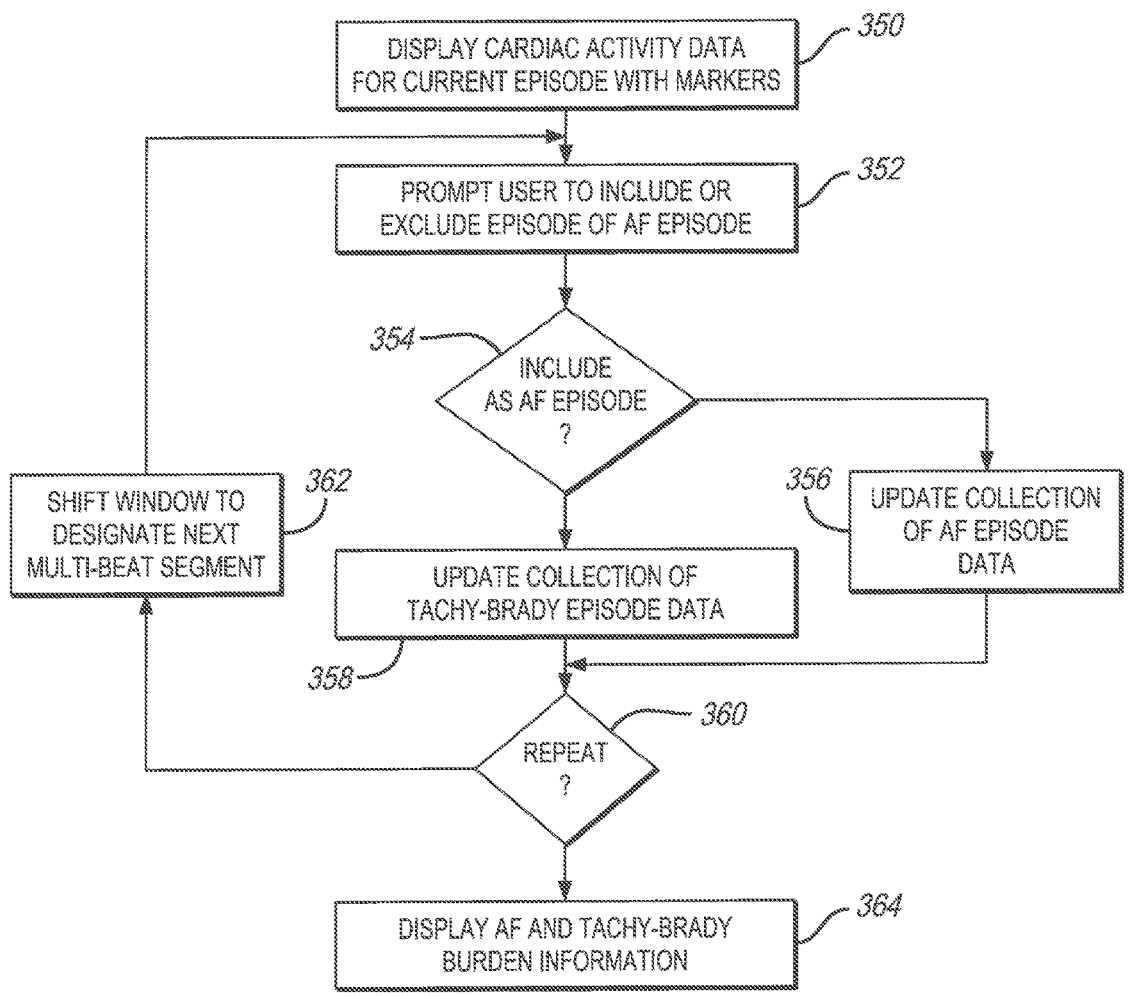
FIG. 3B illustrates a process for obtaining physician feedback to indicate whether Tachy-Brady episodes should be included within an AF episode data collection in accordance with embodiments herein.

FIG. 3B illustrates a process for obtaining physician feedback to indicate whether Tachy-Brady episodes should be included within an AF episode data collection in accordance with embodiments herein. At 350, one or more processors, obtains from memory, cardiac activity data along with markers and other information (e.g. time/date stamp for the start/end times of the episode, duration of the episode, severity of the episode, etc.) indicative of AF and/or Tachy-Brady episodes. At 350, the processor directs a display to display the cardiac activity data for the current episode (e.g. AF and/or Tachy-Brady episodes), along with the markers. As explained above in connection with FIGS. 3A and 4, the markers include rhythm patterns transition markers to illustrate to the physician the point at which a rhythm pattern changed between fast and slow patterns. At 350, the cardiac activity data may be presented for multiple episodes, such as the ECG signal illustrated in FIG. 4.

At 352, a multi-beat segment within the cardiac activity data is designated. For example, with respect to FIG. 4, a bracket (e.g. such as bracket 410) may be presented on the display or a window (e.g. such as window 414) may be presented on the display. In connection with presenting the bracket 410 or window 414, the user is prompted to indicate whether the current multi-beat segment should be included or excluded as an AF episode.

At 354, the user input is analyzed. When the current multi-beat segment is designated to be included as an AF episode, flow branches to 356. Otherwise, flow branches to 358. At 356, the processor updates a data collection concerning AF episodes. By way of example, the episode data related to the current multi-beat session is added to the collection of AF episodes and the present multi-beat session is designated to represent an AF episode. At 358, the processor updates a data collection related to Tachy-Brady episodes. By way of example, the episode data related to the current multi-beat session is added to the collection of Tachy-Brady episodes in the present multi-beat session is designated to represent a Tachy-Brady episode. The data collections may include various information describing each AF or Tachy-Brady episode, including but not limited to, a date/time stamp for the beginning/end of the episode, a duration of the episode, other information regarding the condition of the patient, such activity data, patient orientation and the like.

Following the operations at 356 and 358, the processor determines (at 360) whether to repeat the foregoing operations in connection with additional multi-beat segments. When additional multi-beat segments are to be processed, flow advances to 362. At 362, the processor shifts the window or bracket to designate the next multi-beat session within the cardiac activity data. For example, with reference to FIG. 4, the processor may shift the window/bracket to correspond to window 415 or bracket 411. Thereafter, flow returns to 352 where the user is prompted again to designate whether the next episode should be included or excluded as an AF episode.

Figure 8:
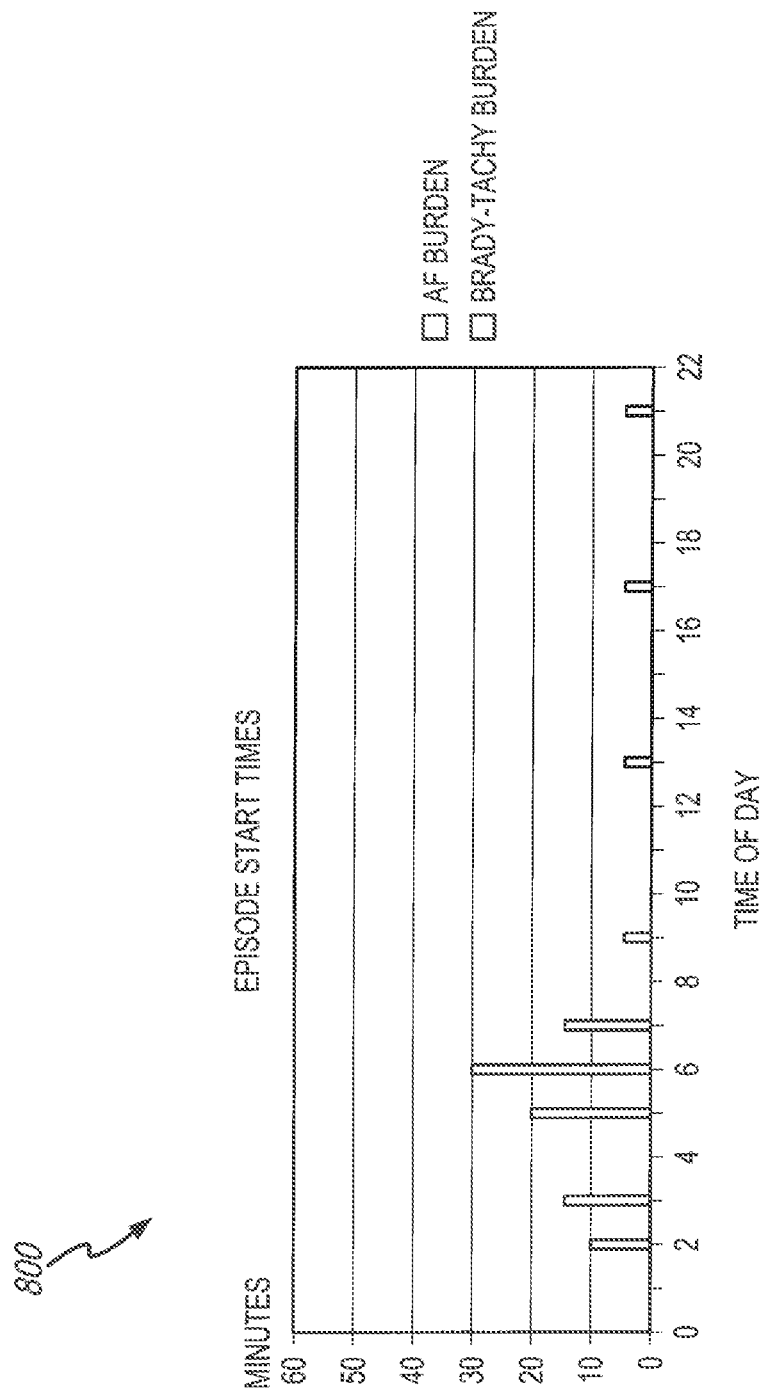
FIG. 8 illustrates a manner in which information related to AF episodes may be presented to a clinician in accordance with embodiments herein.

Returning to 360, when it is determined that no additional multi-beat sessions are to be analyzed, flow advances to 364. At 364, the processor directs the display to display various types of information, such as burden related information. By way of example, at 364, AF burden information may be presented to the physician. Additionally or alternatively, at 364, Tachy-Brady burden information may be displayed to the physician (e.g. as illustrated in FIGS. 7 and 8).While the foregoing process illustrates the operation at 364 in connection with the operations at 350-360, it is recognized that the display operation at 364 may be performed entirely independent of the operations at 350-360.

Figure 5:
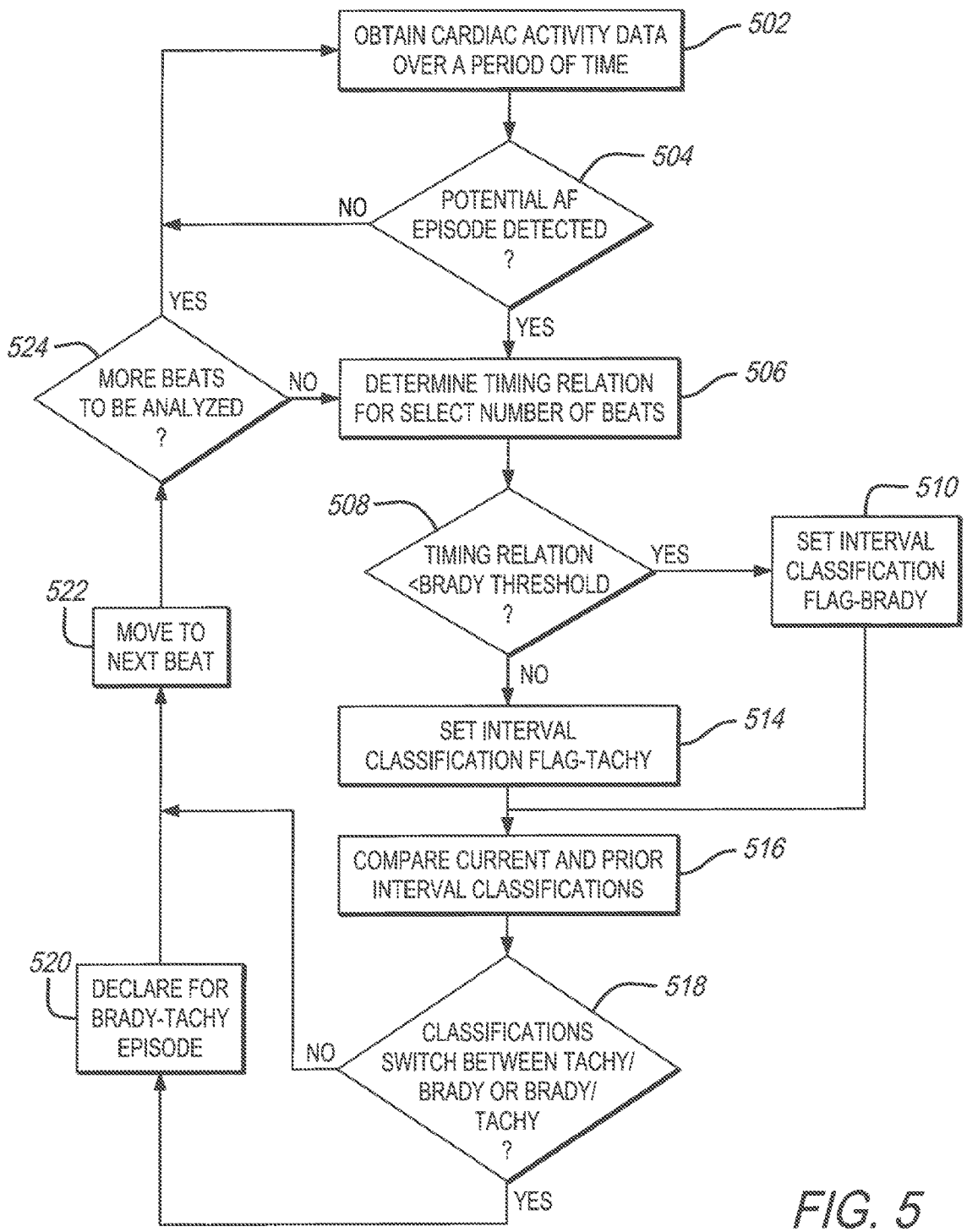
FIG. 5 illustrates a computer implemented process for discriminating rhythm patterns of interest in cardiac activity in accordance with embodiments herein.

FIG. 5 illustrates a computer implemented process for discriminating rhythm patterns of interest in cardiac activity in accordance with embodiments herein. The operations of FIG. 5 may be repeated periodically or in response to detection of particular criteria, such as detection of potential atrial fibrillation episodes or otherwise. As one example, the cardiac activity data may be collected for a one minute interval, during which multiple successive cardiac beats occur.

Figure 6:
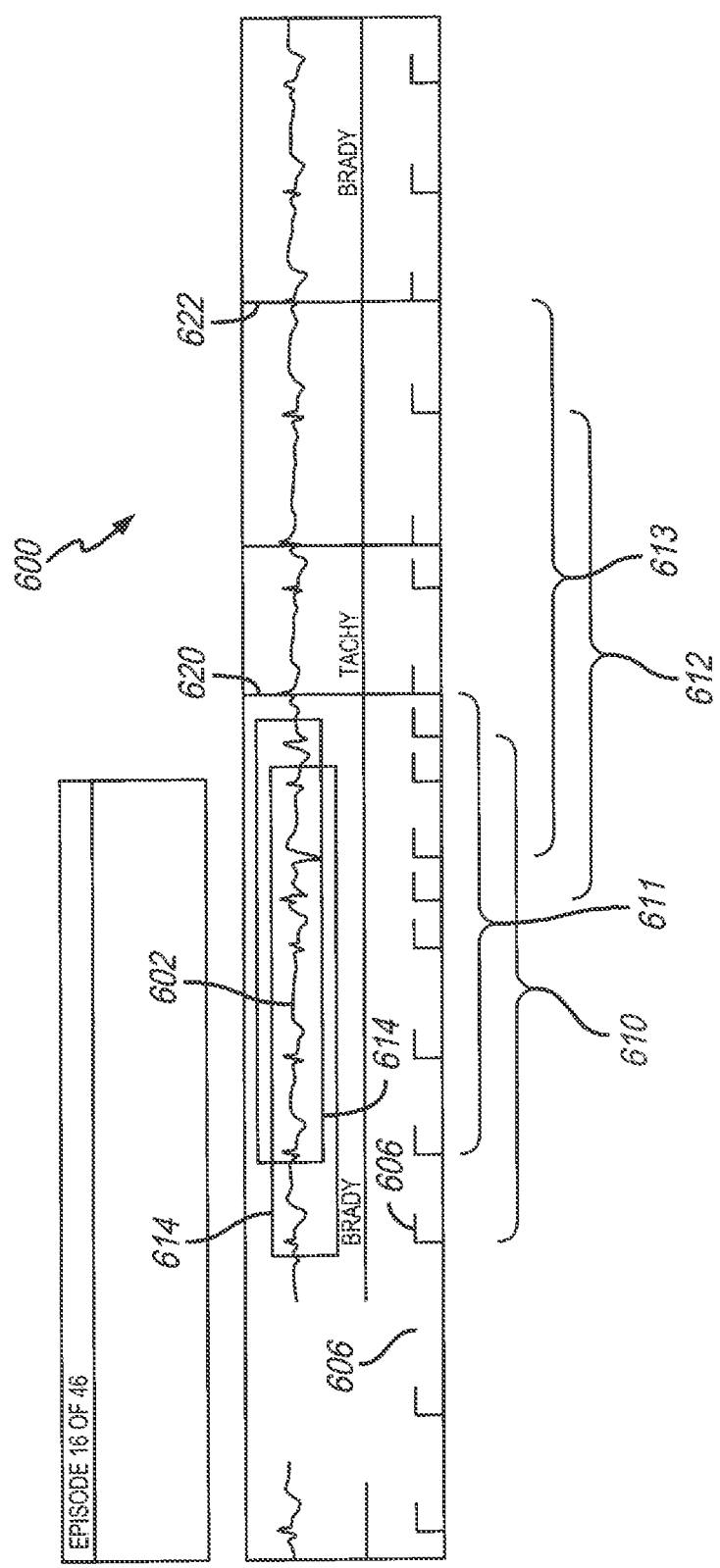
FIG. 6 illustrates an example of the cardiac activity data that may be collected by an implantable cardiac monitor for a portion of a predetermined period of time in accordance with embodiments herein.

At 502, one or more processors obtain cardiac activity data for multiple cardiac beats over a predetermined period of time. FIG. 6 illustrates an example of the cardiac activity data that may be collected by an implantable cardiac monitor for a portion of a predetermined period of time. FIG. 6 illustrates an example of a display 600 that presents cardiac activity data 602, as well as related markers and other content are presented to a clinician on a display. The cardiac activity data 602 is displayed as EGM signals relative to a timeline. The EGM signals correspond to ventricular activity sensed by the implantable cardiac monitor, and are annotated with ventricular sensing (VS) markers 604 indicating a time at which ventricular events were detected. A beat to beat interval 606 is presented to illustrate the time interval between successive VS markers 604. Multi-beat segments 610-613 overlap. A length of the multi-beat segment 610-613 is determined by measurement windows 614 that are used collect cardiac beats timing relations of interest that characterize the interrelation of the cardiac beats within the corresponding multi-beat segments. In the example of FIG. 6, the measurement windows 614 each include eight cardiac beats.

Returning to FIG. 5, at 504, one or more processors analyze the cardiac activity data to determine whether a potential AF episode has been detected (e.g. in accordance with the process described in U.S. Pat. No. 8,135,456 or another AF detection algorithm). When no potential AF episode is detected, the cardiac activity data need not be further analyzed for abnormal rhythm patterns and flow returns to 502. Alternatively, when a potential AF episode is detected, flow advances to 506. At 506, a processor calculates a cardiac beats timing relation representative of intervals between the cardiac beats within the current measurement window.

The process of FIG. 5 differs, at least in part, from the process of FIG. 3A in that the process of FIG. 5 utilizes a single rate threshold, instead of separate Brady and Tachy thresholds. At 508, the processor compares the cardiac beats timing relation to a single rate threshold. The rate threshold may be programmed by a clinician or automatically determined and adjusted by the monitoring device throughout operation. By way of example, the rate threshold may represent a limit that distinguishes Brady/slow activity from Tachy/fast activity. For example, the rate threshold may be set at 75 beats per minute (bpm). When a multi-beat segment exhibits an interval average for the beat to beat interval below 75 bpm, the corresponding rhythm pattern is considered to represent a slow or Brady rhythm pattern. Accordingly, flow branches to 510. Alternatively, when a multi-beat segment exhibits an interval average above 75 bpm, the corresponding rhythm pattern is considered to represent a fast or Tachy rhythm pattern. Accordingly, flow branches to 514.

At 510, the processor sets an interval classification characterizing the multi-beat segment as slow or Brady. At 514, the processor sets an interval classification characterizing the multi-beat segment as fast or Tachy. The operations at 510 and 514 designate the cardiac beats timing relation to have an irregular rhythm pattern of interest based on the rate threshold.

Following the operations at 510 or 514, flow advances to 516. At 516 and 518, the processor identifies when successive multi-beat segments exhibit an irregular rhythm pattern transition between fast and slow rhythm patterns. At 516, the processor compares interval classifications (e.g. flags) that were set in connection with current and prior multi-beat segments. At 518, the processor determines whether the interval classification, corresponding to the current and prior multi-beat segments, differ from one another and represent a change between fast and slow irregular rhythm patterns. When the interval classification changes, flow branches to 520. When the interval classification does not change, flow branches to 522.

At 520, the processor declares the cardiac activity data to exhibit a Tachy-Brady episode and records information indicative of the Tachy-Brady episode in connection with the cardiac activity data. For example, at 520, the processor records/saves in memory the rhythm patterns transition in connection with the cardiac activity data.

At 522, the processor steps to the next cardiac beat. At 524, the processor determines whether any additional cardiac beats remain to be analyzed in connection with the present set of cardiac activity data. When additional cardiac beats remain to be analyzed, flow moves from 524 to 506 and the above-described process is repeated for the next multi-beat segment. Otherwise, flow returns to 502 and a new cardiac activity data set is obtained.

With reference to FIG. 6, the process of FIG. 5, would identify rhythm patterns transitions at markers 620 and 622. The multi-beat segment 610 includes an interval average corresponding to a slow rhythm pattern, while the multi-beat segment 611 corresponds to a fast rhythm pattern. Accordingly, an rhythm patterns transition marker 620 would be designated to reflect the corresponding transition between rhythm patterns. Shortly thereafter, the patient experiences an additional rhythm patterns transition from a fast rhythm pattern back to a slow rhythm pattern. Specifically, the multi-gate segment 612 exhibits a fast rhythm pattern, while the following multi-gate segment 613 exhibits a slow rhythm pattern. Accordingly, and rhythm patterns transition marker 622 would be designated on the cardiac activity data displayed.

As noted above, when Tachy-Brady episodes are identified, corresponding information may be recorded in memory. By way of example, the number of Tachy-Brady episodes may be recorded in a manner similar to recording of AF episodes. Optionally, a display may present information indicative of Tachy-Brady burden over time in combination with information indicative of AF burden over time. For example, AF episodes and Tachy-Brady episodes may be counted over predetermined periods of time (e.g. hourly, daily, weekly etc.). The AF episodes and Tachy-Brady episodes may be utilized to illustrate AF and Tachy-Brady burden that may be presented in various formats, such as in a histogram format.

FIG. 7 illustrates an example of one manner by which AF burden and Tachy-Brady burden information may be presented to a clinician. For example, a display may be configured to display the information of FIG. 7 as Tachy-Brady burden formatted to present an amount of time, during which the cardiac activity data experienced Tachy-Brady episodes. In FIG. 7, an AF histogram 702 and a Tachy-Brady histogram 704 are presented in a time aligned manner with respect to one another. The horizontal axis of the histograms 702, 704 correspond to a temporal interval of interest. In the example of FIG. 7, the horizontal axis corresponds to successive days over a period of time, during which cardiac activity data is collected. For example, 16 successive days are illustrated. The histograms illustrate, along the vertical axis, a count of the number of episodes of the corresponding type that were recorded during the associated day. For example, on day three, five Tachy-Brady episodes were recorded as indicated at 706. As another example, 10, 11 and 12 Tachy-Brady episodes were detected on days six, seven and eight, respectively. Thereafter, AF episodes were detected on days nine through 16. For example, one AF episode was detected on day nine, two AF episodes were detected on day 10 and four AF episodes were detected on day 11.

In accordance with embodiments herein, the AF and Tachy-Brady burden information may be co-displayed (e.g. as in the manner illustrated in FIG. 7 or another manner). For example, co-displaying the AF and Tachy-Brady burden information may illustrate that, before the patient experiences more persistent and longer durations of AF episodes, the patient experiences a precursor of Tachy-Brady episodes (e.g., an indication of early onset of AF, such as runs of Premature Atrial Beats, etc.). As the patient's disease progressed, the number of Tachy-Brady episodes decreased (e.g. the Tachy-Brady burden reduced), while the number of AF episodes increased and the AF burden ramped up. It is well known that "AF begets AF", and the earlier AF is caught and treated, the better the patient outcomes will be. Advantageously, the Tachy-Brady Burden is precursor to AF and embodiments herein facilitate earlier detection and early treatment. It is recognized that the information illustrated in FIG. 7 and the manner/format in which such information is presented is merely by way of example and is not limiting upon the embodiments herein.

FIG. 8 illustrates an alternate or supplemental manner in which information related to AF episodes may be presented to a clinician. For example, the graph 800 of FIG. 8 may be presented on a display of various computing devices to the physician. The graph 800 illustrates hourly occurrences of AF and Tachy-Brady episodes. FIG. 8 formats the AF and Tachy-Brady episodes in a manner to present daily burden information. The Tachy-Brady daily burden presents the start times of the episodes and the amount of time that the patient was in a Tachy-Brady state at the corresponding start times, during which the cardiac activity data experienced Tachy-Brady episodes. The AF daily burden presents the start times of the episodes and the amount of time that the patient was in an AF state at the corresponding start times, during which the cardiac activity data experienced AF episodes. The graph 800 illustrates start times over the course of a day at which AF episodes and Tachy-Brady episodes initiated. In FIG. 8, the horizontal axis indicates the time of day, while the vertical axis indicates the amount of time during which a corresponding episode persisted. For example, at 2 AM, the patient experienced a Tachy-Brady episode that lasted 10 minutes. At 6 AM, the patient experienced an AF episode that lasted 30 minutes. The patient experienced additional Tachy-Brady episodes at 9 AM, 1 PM, 5 PM and 11 PM, each of which lasted/persisted for approximately 5 minutes.

The information in FIG. 8 may correspond to a single day. Alternatively, the episode related information in FIG. 8 may be collected over multiple days. When the information is collected over multiple days, the information presented may correspond to an average or some other combination of the episode related information in connection with each time of day.

It is recognized that the information in FIG. 8 is hypothetical and that patients may have more AF episodes or fewer Tachy-Brady episodes than illustrated. By way of example, the patient may experience multiple AF episodes in the early hours of the morning. The information presented in FIGS. 4 and 6-8 may be displayed on the display of an external device, laptop or desktop computer, workstation, phone, personal digital assistant, tablet device, etc.

As one example, the hourly occurrence information (as shown in FIG. 8) may be utilized to indicate that a patient's medication (for suppressing AF episodes) is wearing off or not otherwise effective at certain times of day. For example, the data may indicate that Tachy-Brady episodes increase in occurrence in the early hours of the morning, before progressing to an AF episode in the early morning. However, the data may further indicate that over the course of the day the patient experiences very few Tachy-Brady episodes and/or AF episodes. The occurrence of excessive Tachy-Brady episodes at certain times of day may be utilized by a clinician to determine whether a patient should adjust a medication schedule and/or type of medication. For example, excessive Tachy-Brady episodes at certain times of day may indicate that medication is ineffective at that time of day or that the medication has worn off over the course of an evening. Displaying Tachy-Brady episode information affords physicians additional information that they may not otherwise have given that the Tachy-Brady episodes occurred while the patient was not experiencing an AF event.

Figure 9:
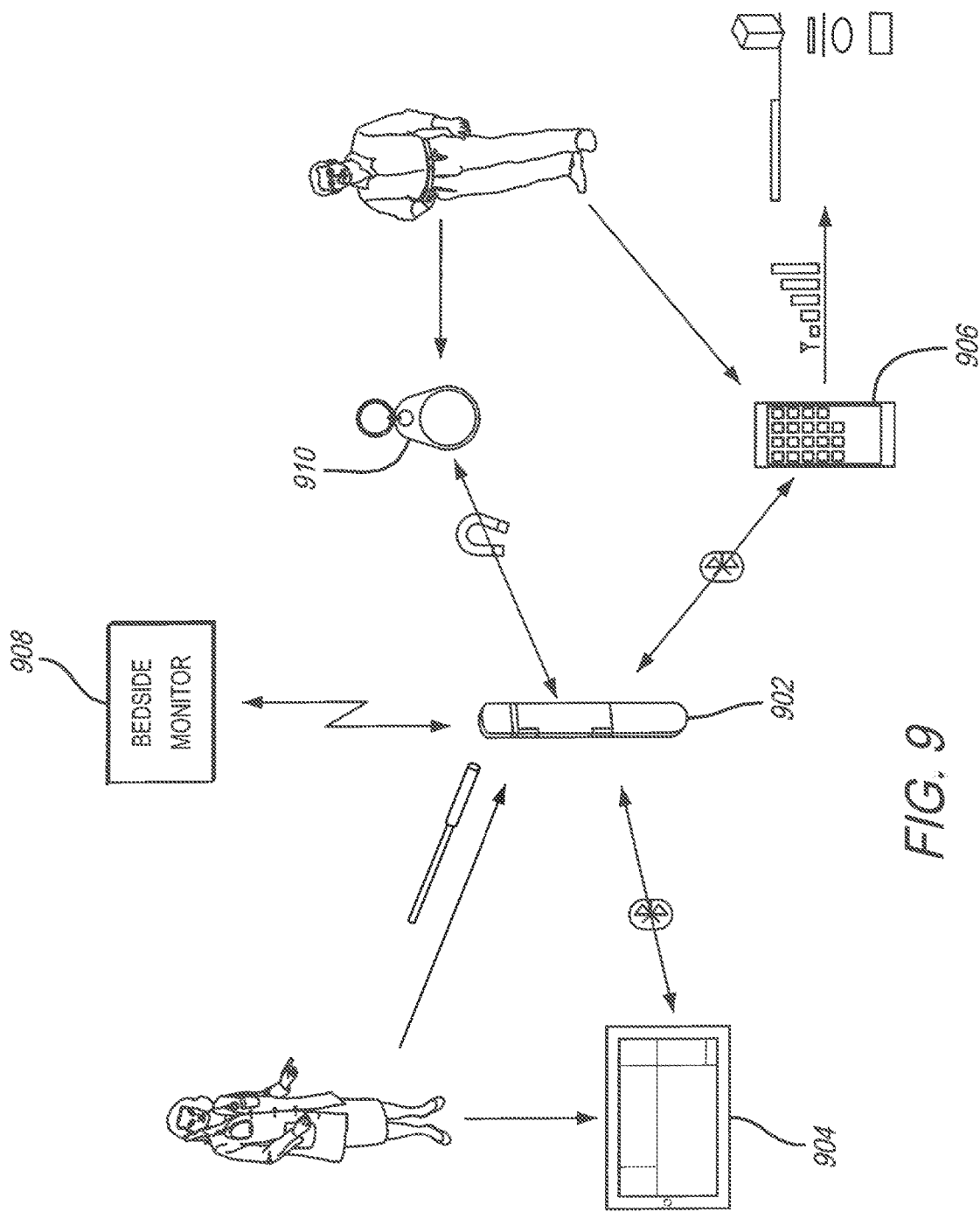
FIG. 9 illustrates a system level diagram indicating potential devices and networks in which the methods and systems herein may be utilized in accordance with embodiments herein.

FIG. 9 illustrates a system level diagram indicating potential devices and networks in which the methods and systems herein may be utilized. For example, an implantable cardiac rhythm monitoring device (ICM) 902 may be utilized to collect cardiac activity data and identify Tachy-Brady episodes therein in accordance with the methods and systems described herein. The ICM 902 may supply the Tachy-Brady event data to various external and internal electronic devices, such as a tablet device 904, a smart phone 906, a bedside monitoring device 908 and the like. The devices 904-908 each include a display to display the various types of information described herein. The ICM 902 may convey the Tachy-Brady event data over various wireless communications links with the devices 904, 906 and 908. The ICM 902 may utilize various communications protocols and be activated in various manners. By way of example only, when a magnetic device 910 is held next to the patient, the magnetic field from the device 910 may activate the ICM 902 to transmit the cardiac activity data and Tachy-Brady event data to one or more of the devices 904-908.

The processes described herein for analyzing the cardiac activity data to identify Tachy-Brady episodes may be implemented on the ICM 902, in which case the Tachy-Brady event data may then be wirelessly conveyed to one or more of the devices 904-908. Additionally or alternatively, the devices 904-908 may also implement the processes described herein to analyze cardiac activity data and identify Tachy-Brady episodes. For example, the ICM 902 may simply convey the raw cardiac activity data for an extended period of time or for discrete periods of time to one or more the devices 904-910. The devices 904-910 then analyze the raw cardiac activity data as described herein.

The devices 904-908 may present the Tachy-Brady event data to clinicians in various manners. As one example, Tachy-Brady markers may be illustrated on EGM signal traces (e.g. as illustrated in FIGS. 4 and 6). Additionally or alternatively, the Tachy-Brady event data may be formatted into histograms or other types of charts to be presented alone or in combination with AF event data (such as illustrated in FIGS. 7 and 8).

Figure 10:
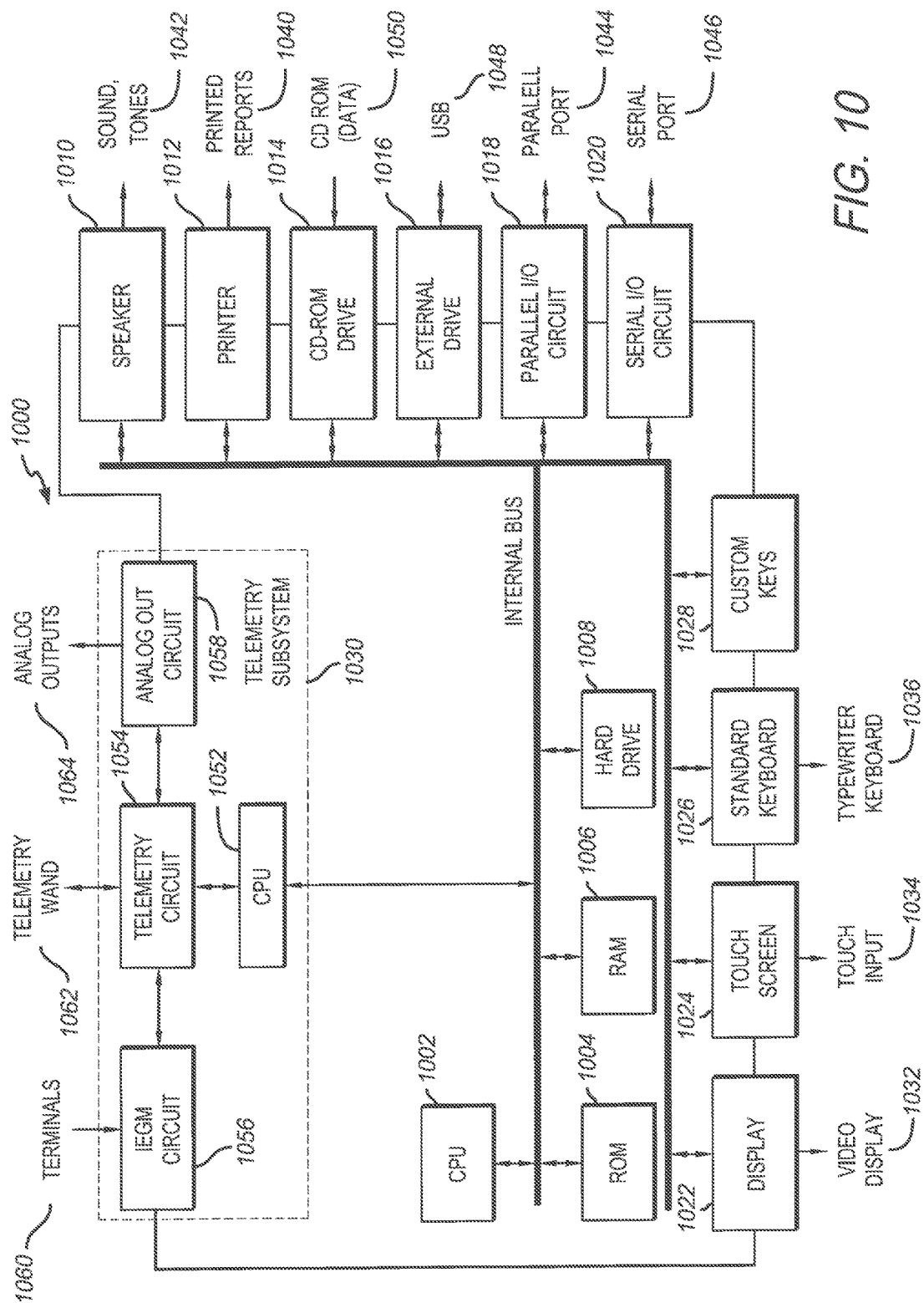
FIG. 10 illustrates a functional block diagram of the external device that is operated in accordance with the processes described herein and to interface with ICMs as described herein.

FIG. 10 illustrates a functional block diagram of the external device 1000 that is operated in accordance with the processes described herein and to interface with ICMs as described herein. The external device 1000 may be a workstation, a portable computer, an ICM programmer, a PDA, a cell phone and the like. The external device 1000 includes an internal bus that connects/interfaces with a Central Processing Unit (CPU) 1002, ROM 1004, RAM 1006, a hard drive 1008, the speaker 1010, a printer 1012, a CD-ROM drive 1014, an external drive 1016, a parallel I/O circuit 1018, a serial I/O circuit 1020, the display 1022, a touch screen 1024, a standard keyboard connection 1026, custom keys 1028, and a telemetry subsystem 1030. The internal bus is an address/data bus that transfers information between the various components described herein. The hard drive 1008 may store operational programs as well as data, such as waveform templates and detection thresholds.

The CPU 1002 typically includes a microprocessor, a micro-controller, or equivalent control circuitry, designed specifically to control interfacing with the external device 1000 and with the ICM or IMD. The CPU 1002 performs the characteristic of interest measurement process discussed above. The CPU 1002 may include RAM or ROM memory, logic and timing circuitry, state machine circuitry, and I/O circuitry to interface with the ICM or IMD. The display 1022 (e.g., may be connected to the video display 1032). The touch screen 1024 may display graphic information relating to the ICM 100. The display 1022 displays various information related to the processes described herein. For example, the display 1022 may display the cardiac activity data (as shown in FIGS. 4 and 6), the burden related information (as shown in FIGS. 7 and 8), as well as additional information. The display 1032 (or a display on a workstation, phone, personal digital assistant, tablet device, etc.) may be configured to display a Tachy-Brady EGM with Tachy-Brady markers indicting transition points in the cardiac activity data. Optionally, the display may be configured to display a Tachy-Brady burden representing an amount of time, daring which the cardiac activity data experienced Tachy-Brady episodes. Optionally, the display may be configured to display a Tachy-Brady Daily burden representing the start times of the episodes and the amount of time in Tachy-Brady at those start times, during which the cardiac activity data experienced Tachy-Brady episodes.

The touch screen 1024 accepts a user's touch input 1034 when selections are made. The keyboard 1026 (e.g., a typewriter keyboard 1036) allows the user to enter data to the displayed fields, as well as interface with the telemetry subsystem 1030. (for example when used in connection with a pacemaker) The printer 1012 prints copies of reports 1040 for a physician to review or to be placed in a patient file, and speaker 1010 provides an audible warning (e.g., sounds and tones 1042) to the user. The parallel I/O circuit 1018 interfaces with a parallel port 1044. The serial I/O circuit 1020 interfaces with a serial port 1046. The external drive 1016 accepts an external devices 1048 (e.g., USB) or other interface capable of communicating with a USB device such as a memory stick. The CD-ROM drive 1014 accepts CD ROMs 1050.

The telemetry subsystem 1030 includes a central processing unit (CPU) 1052 in electrical communication with a telemetry circuit 1054, which communicates with both an EGM circuit 1056 and an analog out circuit 1058. The circuit 1056 may be connected to terminals 1060. The terminals 1060 are also connected to the implantable electrodes 114, 116 and 118 to receive and process EGM cardiac signals as discussed above. Optionally, the EGM cardiac signals sensed by the electrodes may be collected by the ICM or IMD and then transmitted, to the external device 1000, wirelessly to the telemetry subsystem 1030 input.

The telemetry circuit 1054 may be coupled to a telemetry wand 1062. The analog out circuit 1058 includes communication circuits to communicate with analog outputs 1064. The external device 1000 may wirelessly communicate with the ICM 100 and utilize protocols, such as Bluetooth, GSM, infrared wireless LANs, HIPERLAN, 3G, satellite, as well as circuit and packet data protocols, and the like.

Figure 11:
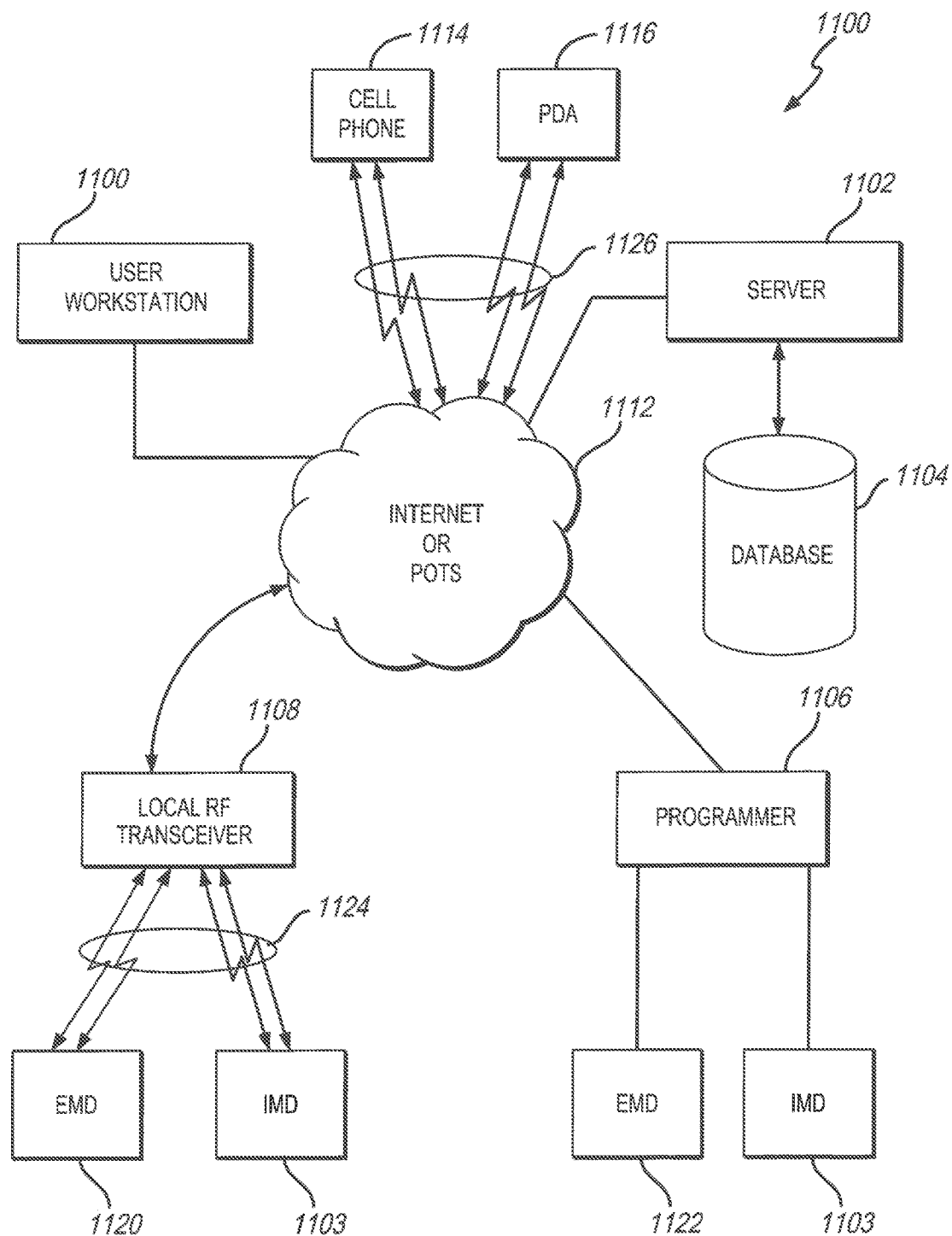
FIG. 11 illustrates a distributed processing system 1100 in accordance with one embodiment.

FIG. 11 illustrates a distributed processing system 1100 in accordance with one embodiment. The distributed processing system 1100 includes a server 1102 connected to a database 1104, a programmer 1106, a local RF transceiver 1108 and a user workstation 1110 electrically connected to a communication system 1112. Any of the processor-based components in FIG. 11 (e.g., workstation 1110, cell phone 1114, PDA 1116, server 1102, programmer 1106, ICM 1103) may perform the characteristic of interest measurement process discussed above.

The communication system 1112 may be the internet, a voice over IP (VoIP) gateway, a local plain old telephone service (POTS) such as a public switched telephone network (PSTN), a cellular phone based network, and the like. Alternatively, the communication system 1112 may be a local area network (LAN), a campus area network (CAN), a metropolitan area network (MAN), or a wide area network (WAM). The communication system 1112 serves to provide a network that facilitates the transfer/receipt of information such as cardiac signal waveforms, ventricular and atrial heart rates.

The server 1102 is a computer system that provides services to other computing systems over a computer network. The server 1102 controls the communication of information such as cardiac activity data, Tachy-Brady episode information, AF episode information, markers, cardiac signal waveforms, ventricular and atrial heart rates, and detection thresholds. The server 1102 interfaces with the communication system 1112 to transfer information between the programmer 1106, the local RF transceiver 1108, the user workstation 1110 as well as a cell phone 1114 and a personal data assistant (PDA) 1116 to the database 1104 for storage/retrieval of records of information. On the other hand, the server 1102 may upload cardiac activity data from surface ECG unit 1120 or the ICM 1103 via the local RF transceiver 1108 or the programmer 1106.

The database 1104 stores information such as cardiac activity data, Tachy-Brady episode information, AF episode information, markers, cardiac signal waveforms, ventricular and atrial heart rates, detection thresholds, and the like, for a single or multiple patients. The information is downloaded into the database 1104 via the server 1102 or, alternatively, the information is uploaded to the server from the database 1104. The programmer 1106 is similar to the external device 600 and may reside in a patient's home, a hospital, or a physician's office. The programmer 1106 interfaces with (e.g. in connection with a pacemaker) the ICM 1103. The programmer 1106 may wirelessly communicate with the ICM 1103 and utilize protocols, such as Bluetooth, GSM, infrared wireless LANs, HIPERLAN, 3G, satellite, as well as circuit and packet data protocols, and the like. Alternatively, a telemetry "wand" connection may be used to connect the programmer 1106 to the ICM 1103. The programmer 1106 is able to acquire cardiac signals from the surface of a person (e.g., ECGs), electrograms (e.g., EGM) signals from the ICM 1103, and/or cardiac activity data, Tachy-Brady episode information, AF episode information, markers, cardiac signal waveforms, ventricular and atrial heart rates, and detection thresholds from the ICM 1103. The programmer 1106 interfaces with the communication system 1112, either via the internet, to upload the information acquired from the surface ECG unit 1120, or the ICM 1103 to the server 1102.

The local RF transceiver 1108 interfaces with the communication system 1112 to upload one or more of cardiac activity data, Tachy-Brady episode information, AF episode information, markers, cardiac signal waveforms, ventricular and atrial heart rates, and detection thresholds 246 (shown in FIG. 2) to the server 1102. In one embodiment, the surface ECG unit 1120 and the ICM 1103 have a bi-directional connection 1124 with the local RF transceiver 1108 via a wireless connection. The local RF transceiver 1108 is able to acquire cardiac signals from the surface of a person, cardiac activity data and other information from the ICM 1103, and/or cardiac signal waveforms, ventricular and atrial heart rates, and detection thresholds from the ICM 1103. On the other hand, the local RF transceiver 1108 may download stored cardiac activity data, Tachy-Brady episode information, AF episode information, markers, cardiac signal waveforms, ventricular and atrial heart rates, and detection thresholds, and the like, from the database 1104 to the surface ECG unit 1120 or the ICM 1103.

The user workstation 1110 may interface with the communication system 1112 via the internet to download cardiac signal waveforms, ventricular and atrial heart rates, and detection thresholds via the server 1102 from the database 1104. Alternatively, the user workstation 1110 may download raw data from the surface ECG units 1120, lead 1122 or ICM 1103 via either the programmer 1106 or the local RF transceiver 1108. Once the user workstation 1110 has downloaded the cardiac signal waveforms, ventricular and atrial heart rates, or detection thresholds, the user workstation 1110 may process the information in accordance with one or more of the operations described above. The user workstation 1110 may download the information and notifications to the cell phone 1114, the PDA 1116, the local RF transceiver 1108, the programmer 1106, or to the server 1102 to be stored on the database 1104. For example, the user workstation 1110 may communicate data to the cell phone 1114 or PDA 1116 via a wireless communication link 1126.

The processes described herein in connection with analyzing cardiac activity data for AF detection and Tachy-Brady episodes may be performed by one or more of the devices illustrated in FIG. 11, including but not limited to the ICM 1103, programmer 1106, user workstation 1110, cell phone 1114, PDA 1116 and server 1102.

Closing

The various methods as illustrated in the Figures and described herein represent exemplary embodiments of methods. The methods may be implemented in software, hardware, or a combination thereof. In various of the methods, the order of the steps may be changed, and various elements may be added, reordered, combined, omitted, modified, etc. Various of the steps may be performed automatically (e.g., without being directly prompted by user input) and/or programmatically (e.g., according to program instructions).

Various modifications and changes may be made as would be obvious to a person skilled in the art having the benefit of this disclosure. It is intended to embrace all such modifications and changes and, accordingly, the above description is to be regarded in an illustrative rather than a restrictive sense.

Various embodiments of the present disclosure utilize at least one network that would be familiar to those skilled in the art for supporting communications using any of a variety of commercially-available protocols, such as Transmission Control Protocol/Internet Protocol ("TCP/IP"), User Datagram Protocol ("UDP"), protocols operating in various layers of the Open System Interconnection ("OSI") model, File Transfer Protocol ("FTP"), Universal Plug and Play ("UpnP"), Network File System ("NFS"), Common Internet File System ("CIFS") and AppleTalk. The network can be, for example, a local area network, a wide-area network, a virtual private network, the Internet, an intranet, an extranet, a public switched telephone network, an infrared network, a wireless network, a satellite network and any combination thereof.

In embodiments utilizing a web server, the web server can run any of a variety of server or mid-tier applications, including Hypertext Transfer Protocol ("HTTP") servers, FTP servers, Common Gateway Interface ("CGI") servers, data servers, Java servers, Apache servers and business application servers. The server(s) also may be capable of executing programs or scripts in response to requests from user devices, such as by executing one or more web applications that may be implemented as one or more scripts or programs written in any programming language, such as Java®, C, C# or C++, or any scripting language, such as Ruby, PHP, Perl, Python or TCL, as well as combinations thereof. The server(s) may also include database servers, including without limitation those commercially available from Oracle®, Microsoft®, Sybase® and IBM® as well as open-source servers such as MySQL, Postgres, SQLite, MongoDB, and any other server capable of storing, retrieving and accessing structured or unstructured data. Database servers may include table-based servers, document-based servers, unstructured servers, relational servers, non-relational servers or combinations of these and/or other database servers.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit ("CPU" or "processor"), at least one input device (e.g., a mouse, keyboard, controller, touch screen or keypad) and at least one output device (e.g., a display device, printer or speaker). Such a system may also include one or more storage devices, such as disk drives, optical storage devices and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.) and working memory as described above. The computer-readable storage media reader can be connected with, or configured to receive, a computer-readable storage medium, representing remote, local, fixed and/or removable storage devices as well as storage media for temporarily and/or more permanently containing, storing, transmitting and retrieving computer-readable information. The system and various devices also typically will include a number of software applications, modules, services or other elements located within at least one working memory device, including an operating system and application programs, such as a client application or web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Various embodiments may further include receiving, sending, or storing instructions and/or data implemented in accordance with the foregoing description upon a computer-readable medium. Storage media and computer readable media for containing code, or portions of code, can include any appropriate media known or used in the art, including storage media and communication media, such as, but not limited to, volatile and non-volatile, removable and non-removable media implemented in any method or technology for storage and/or transmission of information such as computer readable instructions, data structures, program modules or other data, including RAM, ROM, Electrically Erasable Programmable Read-Only Memory ("EEPROM"), flash memory or other memory technology, Compact Disc Read-Only Memory ("CD-ROM"), digital versatile disk (DVD) or other optical storage, magnetic cassettes, magnetic tape, magnetic disk storage or other magnetic storage devices or any other medium which can be used to store the desired information and which can be accessed by the system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the invention as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including" and "containing" are to be construed as open-ended terms (i.e., meaning "including, but not limited to,") unless otherwise noted. The term "connected," when unmodified and referring to physical connections, is to be construed as partly or wholly contained within, attached to or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

All references, including publications, patent applications and patents, cited herein are hereby incorporated by reference to the same extent as if each reference were individually and specifically indicated to be incorporated by reference and were set forth in its entirety herein.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and physical characteristics described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

What is claimed is:

1. A computer implemented method for discriminating rhythm patterns in cardiac activity, comprising:

under control of one or more processors configured with specific executable instructions, obtaining cardiac activity data for multiple cardiac beats over a predetermined period of time, wherein multi-beat segments within the cardiac activity data exhibit different rhythm patterns of interest including fast and slow irregular rhythm patterns;

calculating a cardiac beat timing relation representative of intervals between the cardiac beats within a measurement window;

designating the cardiac beats timing relation to have one of the rhythm patterns of interest based on a rate threshold;

identifying when successive multi-beat segments exhibit a rhythm pattern transition between the fast and slow irregular rhythm patterns; and recording the rhythm patterns transition in connection with the cardiac activity data.

2. The method of claim 1, further comprising, based on the rhythm patterns transition, declaring the cardiac activity data to exhibit a Tachy-Brady episode and recording information indicative of the Tachy-Brady episode in connection with the cardiac activity data.

3. The method of claim 1, further comprising declaring the cardiac activity data to exhibit a Tachy-Brady episode when at least two rhythm patterns transitions are identified between the fast and slow irregular rhythm patterns.

4. The method of claim 1, wherein the successive multi-beat segments include first and second multi-beat segments, the first multi-beat segment having one of the fast or slow irregular rhythm patterns, the second multi-beat segment having another of the fast or slow irregular rhythm patterns.

5. The method of claim 1, further comprising displaying the cardiac activity data on a display as an electrocardiogram signal over time, and displaying a Tachy-Brady episode marker at a point along the electrocardiogram signal corresponding to the rhythm patterns transition between the fast and slow irregular rhythm patterns.

6. The method of claim 1, wherein the rhythm patterns transition represents a change from a first multi-beat segment having a slow irregular rhythm pattern to a second multi-beat segment having a fast irregular rhythm pattern.

7. The method of claim 1, wherein the rhythm patterns transition represents a change from a first multi-beat segment having a fast irregular rhythm pattern to a second multi-beat segment having a slow irregular rhythm pattern.

8. The method of claim 1, further comprising recording a plurality of rhythm patterns transitions over time and based thereon calculating and displaying a Tachy-Brady burden associated with the cardiac activity data, the Tachy-Brady burden representing an amount of time, during which the cardiac activity data experiences Tachy-Brady episodes.

9. The method of claim 1, wherein the calculating operation includes determining an interval average for beat to beat intervals associated with the multi-beat segment.

10. The method of claim 1, wherein the designating operation includes comparing the cardiac beats timing relation to the rate threshold.

11. The method of claim 1, wherein the rate threshold includes a bradycardia threshold and a tachycardia threshold, the designating operation includes comparing the cardiac beats timing relation to at least one of the bradycardia or tachycardia thresholds in connection with designating the current cardiac beats timing relation to represent a fast, normal or slow irregular rhythm pattern.

12. A system for discriminating rhythm patterns in cardiac activity, the system comprising:

means for obtaining cardiac activity data for multiple cardiac beats over a predetermined period of time, wherein multi-beat segments within the cardiac activity data exhibit different rhythm patterns of interest including fast and slow irregular rhythm patterns;

means for calculating a cardiac beat timing relation representative of intervals between the cardiac beats within a measurement window;

means for designating the cardiac beats timing relation to have one of the rhythm patterns of interest based on a rate threshold;

means for identifying when successive multi-beat segments exhibit a rhythm pattern transition between the fast and slow irregular rhythm patterns;

means for recording the rhythm patterns transition in connection with the cardiac activity data; and means for transmitting at least one of the cardiac activity or the rhythm patterns transition to an electronic device.

\* \* \* \* \*